US012740738B2

(12) United States Patent
Pahlevan et al.

(10) Patent No.: US 12,740,738 B2
(45) Date of Patent: Sep. 22, 2026

(54) NONINVASIVE CARDIOVASCULAR EVENT DETECTION

(71) Applicant: UNIVERSITY OF SOUTHERN CALIFORNIA, Los Angeles, CA (US)

(72) Inventors: Niema M. Pahlevan, Los Angeles, CA (US); Rashid Alavi Dehkordi, Los Angeles, CA (US)

(73) Assignee: UNIVERSITY OF SOUTHERN CALIFORNIA, Los Angeles, CA (US)

(*) Notice: Subject to any disclaimer, the term of this patent is extended or adjusted under 35 U.S.C. 154(b) by 436 days.

(21) Appl. No.: 18/249,952

(22) PCT Filed: Oct. 21, 2021

(86) PCT No.: PCT/IB2021/059733
§ 371 (c)(1),
(2) Date: Apr. 20, 2023

(87) PCT Pub. No.: WO2022/084923
PCT Pub. Date: Apr. 28, 2022

(65) Prior Publication Data

US 2023/0404488 A1 Dec. 21, 2023

Related U.S. Application Data

(60) Provisional application No. 63/111,798, filed on Nov. 10, 2020, provisional application No. 63/094,467, filed on Oct. 21, 2020.

(51) Int. Cl.
*A61B 5/363* (2021.01)
*A61B 5/00* (2006.01)
(Continued)

(52) U.S. Cl.
CPC ............ *A61B 5/363* (2021.01); *A61B 5/0205* (2013.01); *A61B 5/02438* (2013.01);
(Continued)

(58) Field of Classification Search
CPC ... A61B 5/363; A61B 5/0205; A61B 5/02438; A61B 5/7267; A61B 5/7282;
(Continued)

(56) References Cited

U.S. PATENT DOCUMENTS

2006/0116593 A1 6/2006 Zhang et al.
2019/0328243 A1* 10/2019 Nemati ................ A61B 5/0205
(Continued)

FOREIGN PATENT DOCUMENTS

CN 103957780 B * 11/2015 ........... A61B 5/7282
CN 110211684 A * 9/2019 ............. G06N 3/084
(Continued)

OTHER PUBLICATIONS

Patent Cooperation Treaty, Written Opinion and International Search Report issued in PCT/IB2021/059733, Jan. 27, 2022, pp. 1-11.
(Continued)

*Primary Examiner* — Michael J Lau
(74) *Attorney, Agent, or Firm* — Pillsbury Winthrop Shaw Pittman LLP

(57) ABSTRACT

The present application relates to using noninvasive techniques to determine whether a patient has experienced a cardiac event. The present application also relates to using noninvasive techniques to determine a size of a myocardial infarction experienced by a patient. In some embodiments, arterial pressure waveforms may be obtained, and from the arterial pressure waveform, a set of cardiac parameters may be extracted. The extracted cardiac parameters may be provided, as input, to the trained machine learning model, which may output a result indicating whether the patient experienced a cardiac event, a size of a myocardial infarction experience by a patient, or other information about the patient's cardiac health.

20 Claims, 18 Drawing Sheets

(51) Int. Cl.

| | |
|---|---|
| ***A61B 5/0205*** | (2006.01) |
| ***A61B 5/024*** | (2006.01) |
| ***G16H 40/67*** | (2018.01) |
| ***G16H 50/20*** | (2018.01) |
| *A61B 5/021* | (2006.01) |
| *A61B 5/145* | (2006.01) |

(52) U.S. Cl.
CPC .......... *A61B 5/7267* (2013.01); *A61B 5/7282* (2013.01); *A61B 5/746* (2013.01); *G16H 40/67* (2018.01); *G16H 50/20* (2018.01); *A61B 5/021* (2013.01); *A61B 5/14542* (2013.01)

(58) Field of Classification Search
CPC ..... A61B 5/746; A61B 5/021; A61B 5/14542; A61B 5/02405; A61B 5/02433; G16H 40/67; G16H 50/20; G16H 40/63; G16H 50/70
See application file for complete search history.

(56) References Cited

U.S. PATENT DOCUMENTS

| | | | | |
|---|---|---|---|---|
| 2020/0108260 | A1 | 4/2020 | Haddad et al. | |
| 2020/0111260 | A1* | 4/2020 | Osborn | A61B 5/6826 |
| 2020/0268252 | A1* | 8/2020 | Litvinova | G06N 3/0495 |

FOREIGN PATENT DOCUMENTS

| | | | | | |
|---|---|---|---|---|---|
| CN | 110693489 | A | | 1/2020 | |
| CN | 111053549 | A | * | 4/2020 | A61B 5/318 |
| EP | 3435858 | B1 | * | 7/2020 | A61B 5/361 |
| WO | WO-2008092215 | A1 | * | 8/2008 | A61B 5/7275 |
| WO | WO-2016092290 | A1 | * | 6/2016 | A61B 5/6898 |
| WO | WO-2018085945 | A1 | * | 5/2018 | A61B 5/02416 |

OTHER PUBLICATIONS

Howard et al., "Artificial Intelligence for Aortic Pressure Waveform Analysis During Coronary Angiography Machine Learning for Patient Safety", JACC: Cardiovascular Interventions, Oct. 28, 2019, pp. 2093-2101, vol. 12 (20).

Armenian et al., "Accuracy of a Novel Handheld Wireless Platform for Detection of Cardiac Dysfunction in Anthracycline-Exposed Survivors of Childhood Cancer", Clinical Cancer Research, Jul. 1, 2018, pp. 3119-3125, vol. 24(13).

Moraes et al., "Advances in Photopletysmography Signal Analysis for Biomedical Applications", Sensors, Jun. 9, 2018, pp. 1-26, Vo. 18(1894).

Pahlevan et al., "Intrinsic frequency for a systems approach to hemodynamic waveform analysis with clinical applications", Journal of the Royal Society, Interface, 2014, pp. 1-10, 11:20140617.

Pahlevan et al., "Noninvasive iPhone Measurement of Left Ventricular Ejection Fraction Using Intrinsic Frequency Methodology", Critical Care Medicine, Jul. 2017, pp. 115-1120, vol. 45(7).

* cited by examiner

| Patient ID | First IF | Second IF | First IF Phase Angle | Second IF Phase Angle | Relative Height of Dicrotic Notch (RHDN) | Envelope Ratio (ER) |
|---|---|---|---|---|---|---|
| ID_0 | ω1_0 | ω2_0 | φ1_0 | φ2_0 | RHDN_0 | ER_0 |
| ID_1 | ω1_1 | ω2_1 | φ1_1 | φ2_1 | RHDN_1 | ER_1 |
| ⋮ | ⋮ | ⋮ | ⋮ | ⋮ | ⋮ | ⋮ |
| ID_N | ω1_N | ω2_N | φ1_N | φ2_N | RHDN_N | ER_N |

NONINVASIVE CARDIOVASCULAR EVENT DETECTION

CROSS-REFERENCE TO RELATED APPLICATIONS

This patent application is the National Phase of International Application No. PCT/IB2021/059733, filed Oct. 21, 2021, which designated the U.S. and that International Application was published under PCT Article 21 (2) in English, which claims the benefit of priority to U.S. Provisional Patent Application No. 63/094,467, titled "Hybrid Artificial intelligence-Intrinsic Frequency Method and Device for Instantaneous Detection of Myocardial Infarction and Ischemia," which was filed on 21 Oct. 2020, and U.S. Provisional Patent Application No. 63/111,798, titled "A Hybrid Artificial Intelligence-Intrinsic Frequency Method and System for Instantaneous Determination of Myocardial Infarction Size," which was filed on 10 Nov. 2020. The entire contents of the foregoing applications are incorporated herein by reference, including all text, tables and drawings in its entirety.

BACKGROUND

1. Description of the Related Art

In 2013, an estimated 8.5 million cases of acute myocardial infarctions (MI) occurred worldwide. The first hour of an acute MI represents a critical opportunity for beneficial therapies. As studies have shown, there is a significant reduction in mortality among patients treated within the first hour. Therefore, it is crucial to develop a new, noninvasive, economical, and instantaneous technique for early detection of hemodynamic signatures of myocardial ischemia, acute MI, or other cardiovascular events. Such a technique could significantly reduce the symptom-to-door time and subsequently improve a patient's outcome.

A diagnosis of myocardial ischemia is traditionally based on clinical (e.g., pain) and ECG criteria (e.g., ST-segment change). However, recording an ECG, even during a myocardial ischemic attack, does not always result in detection of the ischemia. While ECG is clearly an important noninvasive and inexpensive test for diagnosis of acute MI or ischemia, ECG neither specific nor definitive of either diagnosis. Furthermore, diagnosis of acute MI or ischemia requires a trained operator to configure sensors on the patient as well as and conduct the ECG test. Other advanced diagnostic techniques/biomarkers, such as myocardial perfusion testing, circulating BNP level, cardiac troponin level, and echocardiography, have been introduced for the detection and assessment of acute MI and ischemia. All of these, however, have limitations, such as invasiveness, radiation exposure, time to receive and analyze data, cost, or other limitations. Still further, diagnosis of acute MI and/or ischemia is a difficult task for any diagnostic tool. Therefore, the use of an alternative methodology can aid in the detection and diagnosis of acute MIs, ischemia, or other cardiac events independently or together with advanced techniques and/or traditional markers of acute MI or ischemia.

In addition to the need for quick, noninvasive, and effective techniques for detect of cardiac events, for certain cardiac events, there is a need to have quick, noninvasive, and effective techniques for determining a mass of necrosis over total LV mass. The mass of necrosis over total LV mass may also be referred herein, interchangeably, as a size or amount of infarcted cardiac tissue or infarct size. A determinant of acute and long-term mortality after myocardial infarction is the (mass of necrosis over total LV mass (e.g., infarct size). In other words, there is a direct relationship between mortality and the extent of infarct size, (e.g., as the myocardium does not have the ability of regeneration). The infarct size also matters for determining how well patients will recover from myocardial infarction. Patients with larger infarcts are more likely to undergo alterations in the structure (dimensions, mass and shape) of the left ventricle, known as cardiac remodeling, which leads to further heart failure. On the other hand, the evaluation of the infarct size is an attractive surrogate end point for the early assessment of new therapies for acute myocardial infarction. Mortality is significantly increased when more than 20% of the left ventricle is infarcted. In addition, accurate determination of the infarct size is necessary to evaluate interventions that may delay the onset of necrosis and/or limit the total extent of infarct size during ischemia/reperfusion. It is of importance to develop new instantaneous, noninvasive, and inexpensive techniques for determination of the infarct size. Such techniques could identify patients at higher risk after myocardial infarction, thereby further intensive monitoring and care can be applied.

Traditionally, the myocardial infarct size (e.g., the mass of necrosis over total LV mass) can be estimated using several techniques such as echocardiography (Echo), nuclear magnetic resonance imaging (MRI), computed tomography (CT), single photon emission computed tomography (SPECT), and positron emission tomography (PET). However, such techniques have several limitations, as detailed above with respect to detection of acute MI and ischemia, including radiation exposure need for expert operators and imaging specialists, time to perform, time to receive and analyze data, need for commercial machine, breath-holding sequences, limited soft-tissue contrast, radiopharmaceuticals, limited observational studies, limitations on metal implants/fragments, and high cost. Therefore, the use of alternative methodology can significantly aid in determining myocardial infarct size independently or together with traditional techniques.

SUMMARY

The following is a non-exhaustive listing of some aspects of the present techniques. These and other aspects are described in the following disclosure.

Some aspects include a machine learning model configured to detect, from cardiac data measured via a client device, whether a patient has experienced one or more cardiac events.

Some aspects include a machine learning model configured to determine, from cardiac data measured via a client device, a size of a myocardial infarction experienced by a patient.

Some aspects include a tangible, non-transitory, machine-readable medium storing instructions that when executed by a computing system cause the computing system to perform operations associated with the aforementioned machine learning models.

Some aspects include a system, including: one or more processors; and memory storing instructions that when executed by the processors cause the processors to effectuate operations associated with the aforementioned machine learning models.

BRIEF DESCRIPTION OF THE DRAWINGS

The above-mentioned aspects and other aspects of the present techniques will be better understood when the present application is read in view of the following figures in which like numbers indicate similar or identical elements.

Figure 1:
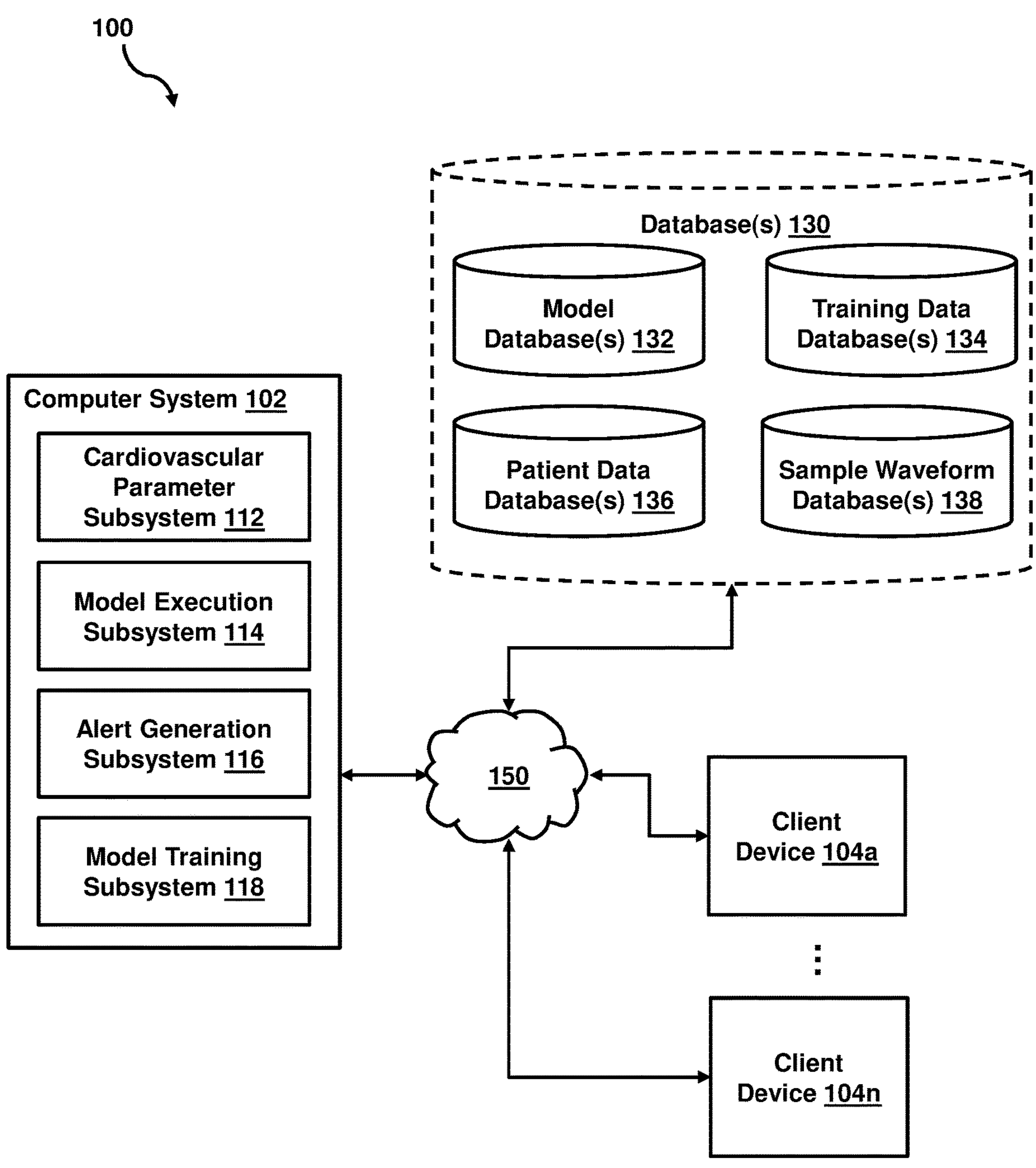
FIG. 1 illustrates an example system for detecting cardiac events and determining a severity of a cardiac event, in accordance with various embodiments.

While the present techniques are susceptible to various modifications and alternative forms, specific embodiments thereof are shown by way of example in the drawings and will herein be described in detail. The drawings may not be to scale. It should be understood, however, that the drawings and detailed description thereto are not intended to limit the present techniques to the particular form disclosed, but to the contrary, the intention is to cover all modifications, equivalents, and alternatives falling within the spirit and scope of the present techniques as defined by the appended claims.

DETAILED DESCRIPTION OF CERTAIN EMBODIMENTS

To mitigate the problems described herein, the inventors had to both invent solutions and, in some cases just as importantly, recognize problems overlooked (or not yet foreseen) by others in the fields of medical-device engineering and machine learning. Indeed, the inventors wish to emphasize the difficulty of recognizing those problems that are nascent and will become much more apparent in the future should trends in the industry continue as the inventors expect. Further, because multiple problems are addressed, it should be understood that some embodiments are problem-specific, and not all embodiments address every problem with traditional systems described herein or provide every benefit described herein. That said, improvements that solve various permutations of these problems are described below.

Millions of individuals experience cases of acute myocardial infarctions (MI), myocardial ischemia, and other cardiac events and illnesses worldwide. Whether someone survives a cardiac event is highly correlated with that individual receiving beneficial therapies quickly, such as within the first hour of onset. Therefore, developing noninvasive, economical, and instantaneous techniques for early detection of hemodynamic signatures of cardiac events, such as myocardial ischemia and acute MI, can significantly reduce the symptom-to-door time and subsequently improve outcomes.

Diagnosing cardiac events, such as acute MI or myocardial ischemia, is traditionally based on clinical (e.g., pain) and ECG (ST-segment change) criteria. However, even if an ECG is performed while an ischemic attack is occurring may not result in the positive detection of the ischemia. While ECGs are clearly an important noninvasive and inexpensive test for diagnosis of acute MI and ischemia, ECGs are neither specific nor definitive. Additionally, ECGs require a trained professional for setup and operation. Other advanced diagnostic techniques/biomarkers such as myocardial perfusion testing, circulating BNP level, cardiac troponin level, and echocardiography have been introduced for the detection and assessment of myocardial ischemia and MI. All these techniques have limitations, such as invasiveness, radiation exposure, time to receive and analyze data, or cost. Regardless, diagnosis of acute MI and myocardial ischemia is a difficult task for any diagnostic tool. Thus, the use of alternative methodology can aid in the diagnosis of myocardial infarction and ischemia independently or together with advanced techniques and/or traditional markers of ischemia.

Integrative systems approaches, such as the Intrinsic frequency (IF) method, that consider the Left Ventricle (LV) and arterial network as a coupled dynamical system (LV+arterial tree) have shown to provide valuable clinical information about the underlying pathology. For instance, as discussed in "Noninvasive iPhone Measurement of Left Ventricular Ejection Fraction Using Intrinsic Frequency Methodology," Pahlevan et al., Critical Care Medicine, 2017; 45:1115-1120, the contents of which is hereby incorporated by reference in its entirety, during a blind clinical study of a heterogeneous adult cohort (n=72), it was demonstrated that the LV ejection fraction (LVEF) (systolic function of the heart) can be accurately evaluated using a smartphone by applying the IF method. As discussed in "Accuracy of a novel handled wireless platform for detection of cardiac dysfunction in anthracycline-exposed survivors of childhood cancer," Armenian et al., Clinical Cancer Research, 2018: In Press, the contents of which are hereby incorporated by reference in its entirety, it was demonstrated that LVEF derived from the IF-iPhone method is more accurate than 2D echocardiogram in childhood cancer survivals (n=191) compared to the costlier gold standard measures obtained from cardiac magnetic resonance (CMR).

Additionally, a determinant of acute and long-term mortality after myocardial infarction is the infarct size (e.g., the mass of necrosis over total LV mass). There is a direct relationship between mortality and the extent of infarct size since the myocardium does not have the ability of regeneration. The infarct size also matters for determining how well patients will recover from myocardial infarction. Patients with larger infarcts are more likely to undergo alterations in the structure (e.g., dimensions, mass, and shape) of the left ventricle, known as cardiac remodeling, which can lead to further heart failure. On the other hand, the evaluation of the infarct size is an attractive surrogate end point for the early assessment of new therapies for acute myocardial infarction. Mortality is significantly increased when more than 20% of the left ventricle is infarcted, so an effective therapy should not let the infarct size go beyond 20%. In addition, accurate determination of the infarct size is necessary to evaluate interventions that may delay the onset of necrosis and/or limit the total extent of infarct size during ischemia/reperfusion. Therefore, developing instantaneous, noninvasive, and inexpensive techniques for determining the size of the infarct can aid in identifying patients at higher risk after myocardial infarction (e.g., by having further intensive monitoring and application of therapeutic care).

Traditionally, the myocardial infarct size (e.g., the mass of necrosis over total LV mass) can be estimated using several techniques such as echocardiography (Echo), nuclear magnetic resonance imaging (MRI), computed tomography (CT), single photon emission computed tomography (SPECT), and positron emission tomography (PET). However, these techniques have several limitations including radiation exposure, need for expert operators and imaging specialists, time to perform, time to receive and analyze data, need for commercial machine, breath-holding sequences, limited soft-tissue contrast, radiopharmaceuticals, limited observational studies, limitations on metal implants/fragments, and high cost. Therefore, the use of alternative methodology can significantly aid in the determination of myocardial infarct size independently of, or together with, traditional techniques.

Table 1 shows different example techniques for determining a size of an infarct.

TABLE 1

| Methods | Advantage | Disadvantage |
|---|---|---|
| Cardiac Markers (lactate dehydrogenase, creatine kinase, troponins) | Low cost<br>Widely available<br>Fast, easy to perform | Frequent false positive values<br>Infarct size is estimated indirectly<br>Correlation between serum markers and infarct size is not tight<br>Area at risk zone cannot be determined |
| Echocardiography | Non-invasive<br>Low-cost operation<br>Repeatable during chronic studies<br>Comparable with TTC | Procurement is expensive<br>Discrimination of viable from non-viable myocardium is difficult<br>Finding of an optimal acoustic window is difficult<br>Limited observational studies<br>Area at risk zone cannot be determined only at early coronary occlusion |
| Magnetic Resonance Imaging (MRI) | Non-invasive<br>Repeatable during chronic studies<br>Comparable with TTC 3D | Expensive<br>Breath-holding sequences during acquisition<br>Poor images with irregular rhythem<br>Limited observational studies<br>Doses and timing of contrast agent is critical<br>Area at risk zone can be determined only at early coronary occulsion |
| Computed Tomography (CT) | Non-invasive, 3D<br>Repeatable during chronic studies | Ionizing radiation<br>Expensive<br>Limited soft tissue contrast<br>Area at risk zone cannot be determined |
| Single Photon Emission Computed Tomography (SPECT) Positron Emission Tomography (PET) | Non-invasive<br>Morphology and function | Expensive<br>Specific radiopharmaceuticals<br>Limited observational studies for validation<br>Area at risk zone cannot be determined |

FIG. 1 illustrates an example system 100 for detecting cardiac events and determining a severity of a cardiac event, in accordance with various embodiments. In some embodiments, system 100 may include computing system 102, client devices 104*a*-104*n* (which may be referred to herein collectively as "client devices 104," and individually as "client device 104"), databases 130, or other components. Computing system 102 and client device 104 may communicate with one another via network 150 (or in some cases, some or all of computing system 102 may be integrated with the client device 104). Although a single instance of computing system 102 is represented within system 100, multiple instances of computing system 102 may be included within system 100, and a single instance is illustrated to minimize obfuscation within FIG. 1. For example, system 100 may include multiple computing systems, or other components.

Network 150 may be a communications network including one or more Internet Service Providers (ISPs). Each ISP may be operable to provide Internet services, telephonic services, or other services, to one or more components of system 100. In some embodiments, network 150 may facilitate communications via one or more communication protocols, such as, TCP/IP, HTTP, WebRTC, SIP, WAP, Wi-Fi (e.g., 802.11 protocol), Bluetooth, radio frequency systems (e.g., 900 MHz, 1.4 GHz, and 5.6 GHz communication systems), cellular networks (e.g., GSM, AMPS, GPRS, CDMA, EV-DO, EDGE, 3GSM, DECT, IS 136/TDMA, iDen, LTE or any other suitable cellular network protocol), infrared, BitTorrent, FTP, RTP, RTSP, SSH, VOIP, or other mechanisms for facilitating communications between components of system 100.

Client device 104 may include one or more processors, memory, communications components, and/or additional components (e.g., display interfaces, input devices, etc.). Client device 104 may include any type of mobile terminal, fixed terminal, or other device. By way of example, client device 104 may include a desktop computer, a notebook computer, a tablet computer, a smartphone, a wearable device, or other client device. Users may, for instance, utilize client device 104 to interact with one another, one or more servers, or other components of system 100. In some embodiments, wearable devices may be physically or wirelessly connected to client device 104. Various examples of wearable devices (e.g., which client devices 104 may be or may be coupled to), include, but are not limited to, which is not to imply that other lists are limiting, smart watches, smart arm bands, smart patches, smart jewelry (e.g., smart earrings, smart necklaces, smart rings, etc.), smart glasses, smart clothing (e.g., shirts, pants, jackets, socks, shoes, braces), or other wearable items. In some embodiments, client devices 104 may be implantable, or coupled to an implantable device, for constant monitoring. In some embodiments, client devices 104 may include, or be in communication with, a wireless device capable of collecting arterial pulse waveforms, a pulse-ox data, phonocardiogram data, magnetic resonance images (MRIs), echocardiograms (ECGs), or other hematological tests. Data captured by a wearable device may be provided to client devices 104 for further processing/analysis and/or client devices 104 may provide the data to computing system 102. Some or all of the operations performed by computing system 102 and/or client devices 104 may, alternatively, be performed locally by the wearable device. Similarly, some or all of the operations may be performed by client devices 104.

Figure 2:
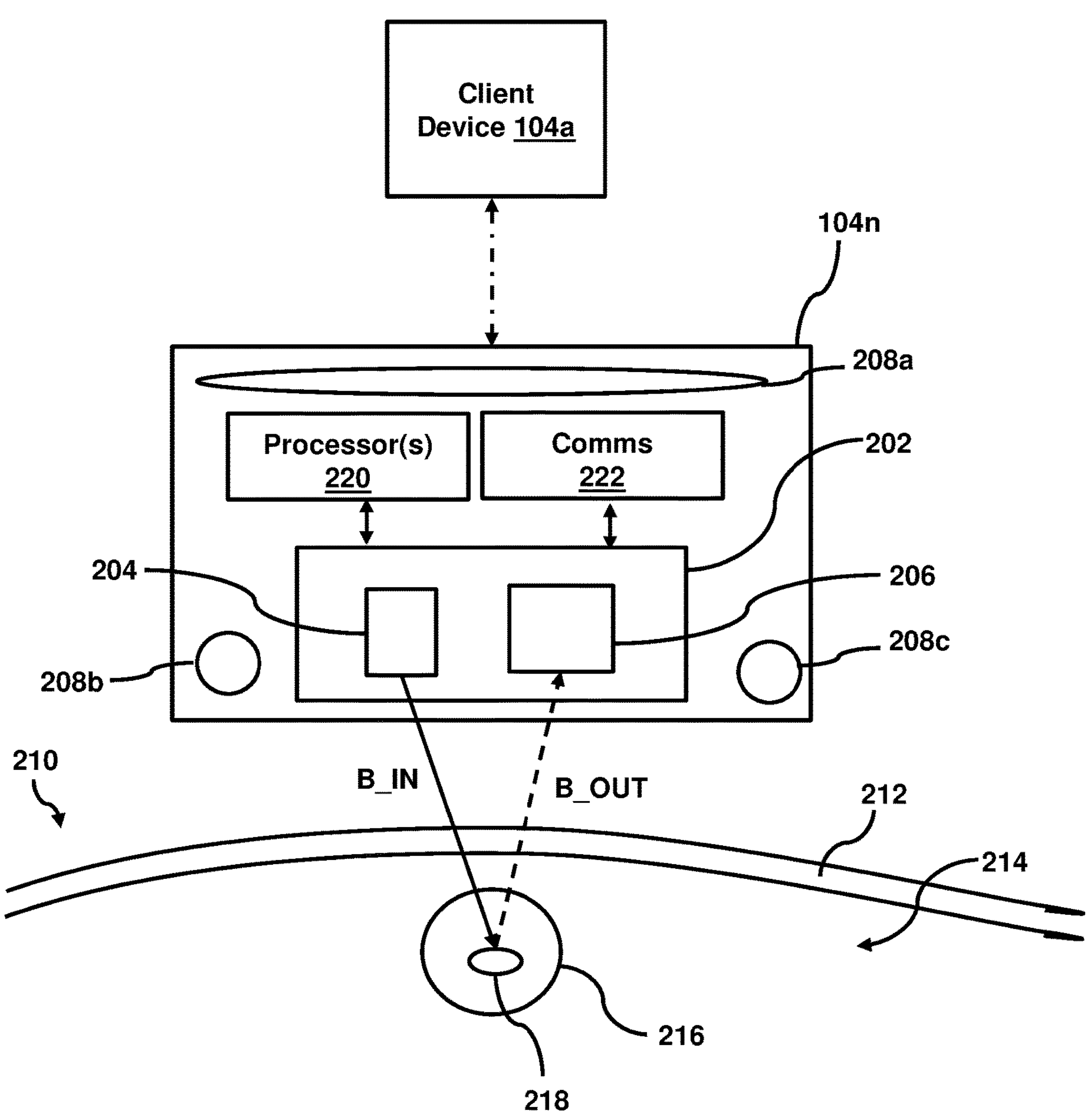
FIG. 2 illustrates an example system for measuring cardiac data of a patient, in accordance with various embodiments.

As an example, with reference to FIG. 2, client device 104*a* may be a non-wearable device (e.g., such as a smartphone, tablet, laptop, etc.) that is physically or wirelessly connected to client device 104*n*, which may be a wearable device, however, alternatively client device 104*n* may not a non-wearable device, such as a pulse measurement device, a smartphone camera, a microwave radar device, or an applanation tonometry device. Client device 104*n* may be configured to capture cardiac data related to a cardiac cycle of a patient. In particular, client device 104*n* may be a wearable device that obtains the cardiac data using non-invasive techniques. The cardiac data may then be transmitted (e.g., via Bluetooth) to client device 104*a* from client device 104*n* for additional analysis/processing. Client device 104*a* may transmit some or all of the cardiac data to computing system 102 for the additional analysis/processing. Persons of ordinary skill in the art will recognize that client device 104*n* need not be a wearable device (e.g., such as, for example, a smartphone), and may be configured to capture and analyze the cardiac data locally.

Client device 104*n* may include one or more instances of photoplethysmography (PPG) sensor 202 for measuring data related to a patient's cardiac activity. For instance, PPG sensor 202 may be configured to measure the patient's heart rate, heart rhythm, or other cardiac information of the patient. While only a single instance of PPG sensor 202 is shown, client device 104*n* may include multiple PPG sensors, or may be communicatively coupled to one or more additional PPG sensors (e.g., located in other client devices or other sensors placed about the patient's body), which may be used together to measure the data related to the patient's cardiac activity.

PPG sensor 202 may include a light source 204, a photodetector 206, or other components. Light source 204 may be an LED capable of emitting light of a particular wavelength/range of wavelengths. For example, light source 204 may be an LED that emits green light with a wavelength of 525 nm, however other wavelengths or ranges of wavelengths may be used. Photodetector 206 may be configured to detect light that reflects or transmits from a patient. PPG sensor 202 may be a transmissive sensor or a reflective sensor. For a reflective sensor, such as that depicted within FIG. 2, light source 204 may emit a beam of light B_IN directed at a portion of a body part 210 of a patient. Beam of light B_IN may pass through one or more layers of skin, such as an upper layer 212 (e.g., stratum corneum, epidermis) and a lower layer 214 (e.g., dermis), into a blood vessel 216 carrying blood. In some cases, beam of light B_IN may reflect off of a red blood cell 218 within the blood carried by blood vessel 216, and the reflected beam of light B_OUT may pass through upper and lower layers 212, 214, and be detected by photodetector 206.

Photodetector 206 may be configured to generate a PPG signal that depends on the flow of blood and the oxygen in each capillary vessel during a given cardiac cycle (e.g., systole and diastole). The PPG signal includes two components: a DC offset representing the constant absorption of light passing through the tissue, and an AC component generated by heartbeats affecting blood volume when light traverses the artery. When there is an increased amount of glucose in the blood, there is a decrease in the misalignment of beam of light B_IN, which causes the refractive index of the tissue to reduce. This results in a smaller amount of light being absorbed, and the light intensity crossing the tissue is greater.

For a transmissive sensor, the light emitted by light source 204 may pass through a portion of a body part 210 of a patient and subsequently be detected by photodetector 206 located on an opposite side of body part 210. For example, light source 204 may be placed on one side of a patient's finger (e.g., on top of a nail), and photodetector 206 may be placed on the opposite side of the patient's finger. The light emitted by light source 204 may pass through the patient's skin pigment, bone, arteries, blood, or other venous features, and may be detected by photodetector 206.

In some embodiments, parameters may be extracted from the PPG signal to analyze heart rate variation (HRV) measurements. The analysis may be performed locally by client device 104*n*, such as by using one or more processors 220 included therein. For example processors 220 may execute computer program instructions to perform operations relating to the analysis of the PPG signal. The results of the analysis may be output, via communications component 222, to client device 104*a*, computing system 102, or other components of system 100. Alternatively, or additionally, the PPG signal may be output by communications component 222 to client device 104*a*, computing system 102, or other components of system 100, for analysis. As summarized below in Table 2, and the parameters may be extracted using linear and/or nonlinear techniques. Additional details related to the linear and nonlinear techniques that may be used to extract parameters for measuring cardiac activity of a patient is provided in "Advances in Photoplethysmography Signal Analysis for Biomedical Applications," Moraes et al., June 2018, DOI: 10.3390/s18061894, Sensors, 18(6), p. 1849, the contents of which are hereby incorporated by reference in their entirety.

TABLE 2

| Technique (Linear/Nonlinear) | Time Domain/ Frequency Domain | Evaluation Indices |
|---|---|---|
| Linear | Time | SDNN, SDANN, $SDNN_i$, rMSSD, pNN50 |
| Linear | Time | RRtri, TINN, Poincare Plot |
| Linear | Frequency | HF, LF, VLF |
| Nonlinear | — | Correlation function, hurst exponent, fractal dimension, Lyapunov exponent |

In some embodiments, PPG sensor 202 may be used to determine a Pulse Transit Time (PPT), which represents a time that a pulse propagates from the heart to a peripheral location. The PTT may also be derived from electrocardiograms (ECGs). PPT has an inverse correlation with blood pressure (BP) and pulse wave velocity (PWV). The PPT may be calculates based on a time interval between a peak of an R wave from the ECG and a peak of a derivative of PPG. For example, the time interval between the peak of the R wave of the ECG and a characteristic point of the PPG in the same cardiac cycle are used to compute the PPT. Thus, client device 104*n* may also include one or more ECG sensors 208*a-c* for capturing ECGs of a patient. ECGs may be captured by measuring changes in electrical signals at the skin's surface generated as the heart beats. In some cases, sensors 208*a-c* may be electrodes used to measure electrical activity at the skin, such as two bottom electrodes (e.g., sensors 208*b*, 208*c*) and one top electrode (e.g., sensor 208*a*), which can be used to obtain ECG signals by measuring a voltage difference between the bottom electrodes (e.g., contacting a left wrist of the patient) and the top electrode (e.g., contacting the right arm). It should also be noted that client device 104 may be configured to capture pulse-oxygen levels of the patient using the same or similar techniques as described above with respect to PPG.

In some embodiments, client device 104 (e.g., a wearable device, a non-wearable device, or a combination of both) may extract features from the ECG/PPG data. The extracted features may indicate a number of heart beats experienced during a given time interval, PPT, a spectrum of PPG, or other features.

Client device 104 may capture a set of arterial blood pressure measurements and may generate an arterial pressure waveform representing the blood pressure measurements. The arterial blood pressure measurements may be computed using measured heart rate (HR) data, pulse-ox data, or other data, as detailed above. The blood pressure measurements may reflect how a patient's blood pressure changes over a given cardiac cycle (e.g., systole and diastole). In some embodiments, multiple blood pressure waveforms over multiple cardiac cycles may be measured/computed by client device 104. The captured blood pressure waveforms may be used to compute an overall blood pressure waveform or may be used for multiple independent analyses.

Figure 3:
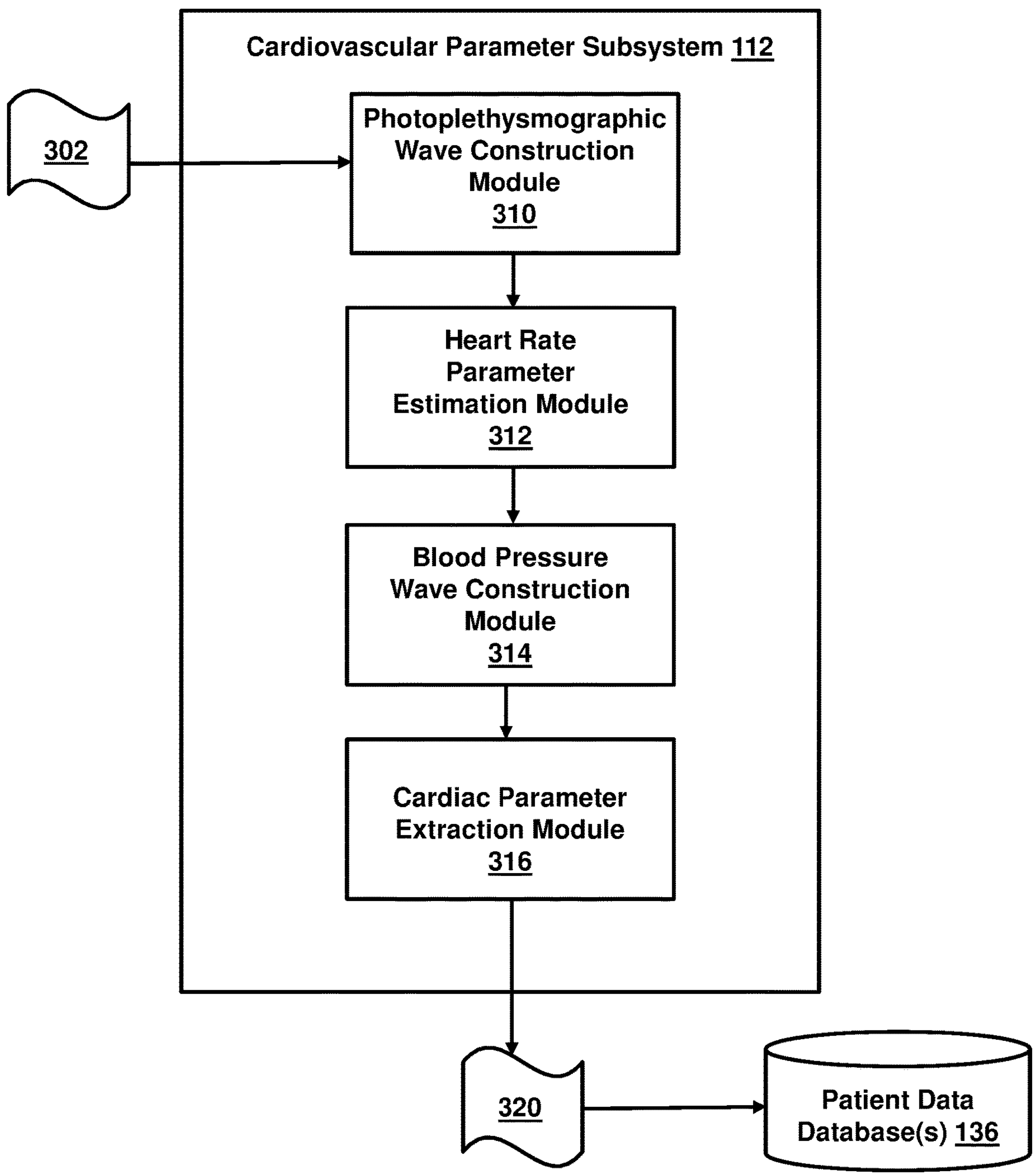
FIG. 3 illustrates an example of a cardiovascular parameter subsystem for obtaining cardiac parameters of a patient, in accordance with various embodiments.

Returning to FIG. 1, cardiovascular parameter subsystem 112 may be configured to extract one or more cardiac parameters from heart rate data. As an example, with reference to FIG. 3, cardiovascular parameter subsystem 112 may be configured to obtain cardiac data 302 from client device 104, a wearable device coupled to client device 104, a data repository, or from other sources. Cardiac data 302 may include heart rate data, heart rate variation data, pulse-ox data, ECG data, PPG data, PTT data, BP data, or other cardiac information related to a cardiac cycle of the patient.

Cardiovascular parameter subsystem 112 may include modules configured to execute tasks related to determining cardiovascular parameters, such as photoplethysmographic (PPG) wave construction module 310, heart rate parameter estimation module 312, blood pressure wave construction module 314, cardiac parameter extraction module 316, or other modules. Each of modules 310-316 may include software that executes certain tasks, and that software may be executed by one or more processors of the corresponding subsystem.

In some embodiments, PPG wave construction module 310 may obtain cardiac data 302 from client device 104, patient data database 136, or other sources. PPG wave construction module 310 may use cardiac data 302 to generate a PPG waveform. Cardiac data 302 may include measurements of changes to blood volume via AC modulations in reflected light (e.g., B_OUT), pulse oxy. Samples of the blood volume captured during a cardiac cycle may include timestamp activity indicating when each measurement was performed. Plotting the PPG signal (e.g., B_OUT) as a function of time may produce a PPG waveform.

In some embodiments, heart rate parameter estimation module 312 may be configured to extract heart rate, PTT, or other aspects of the patient's cardiac cycle from the PPG waveform. The PPG waveform may form a distinct pattern of diastole and systole. An amount of time between consecutive portions of the cardiac cycle can be used to compute heart rate. For example, an amount of time between a beginning of consecutive systole phases can be used to measure a heart rate of the patient's cardiac cycle. In some embodiments, multiple time intervals (e.g., each associated with a measured amount of time between specific phases of the cardiac cycle) may be captured by the PPG waveform. Some cases include averaging, weighting, or performing other statistical combinatory techniques to determine the amount of time between consecutive portions of a cardiac cycle. The amount of time indicates a heart rate of the patient. Heart rate parameter estimation module 312 may generate and output heart rate data indicating the computed heart rate of the patient for a given cardiac cycle. Heart rate parameter estimation module 312 may also compute a pulse transit time (PTT), indicating an amount of time that it takes for a pulse wave to travel between two arterial sites. A speed of the arterial pressure wave, determined based on the distance between the two arterial sites and the PTT, is directly proportional to a patient's blood pressure. Thus, in addition to the heart rate data, heart rate parameter estimation module 312 may generate an output PTT data.

Blood pressure wave (BPW) construction module 314 may be configured to convert the heart rate data to pressure data, and based on the pressure data, may generate an arterial pressure waveform for a cardiac cycle of the patient. As mentioned before, the PTT data and the heart rate data are related to the blood pressure (BP). For example, the PTT is inversely proportional to BP. In some embodiments, BPW construction module 314 may compute a pulse wave velocity (PWV) based on the PTT data. Using the PWV, the blood pressure of the patient may be determined. As an example, the Frank/Bramwell-Hill equation indicates a relationship between PWV and arterial pressure, as indicated by Equation 1:

$$PWV = \sqrt{\frac{VdP}{\rho dV}}. \quad \text{Equation 1a}$$

In Equation 1a, r represents a radius of the arterial vessel, V is the volume per unit length of the arterial vessel, ρ is the blood density, and P is the blood pressure. Alternatively, or additionally, the Moens-Korteweg equation can be used to compute blood pressure from PWV, as seen in Equation 1b:

$$PWV = \sqrt{\frac{Eh}{2r\rho}}. \quad \text{Equation 1b}$$

In Equation 1b, E is the Young's modulus, r is the radius, and h is the vessel thickness. It should be noted that other techniques may be used to compute the BP, such as changes in arterial wall size, pulse rate (e.g., via pulse-ox sensors), or other techniques. Thus, for the PWV determined for the cardiac cycle of the patient, the blood pressure waveform may be obtained. BPW construction module 314 may generate and output BP waveform data representing the BP waveform.

Figure 4:
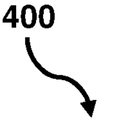
FIG. 4 illustrates an example arterial pressure waveform, in accordance with various embodiments.
Figure 4:
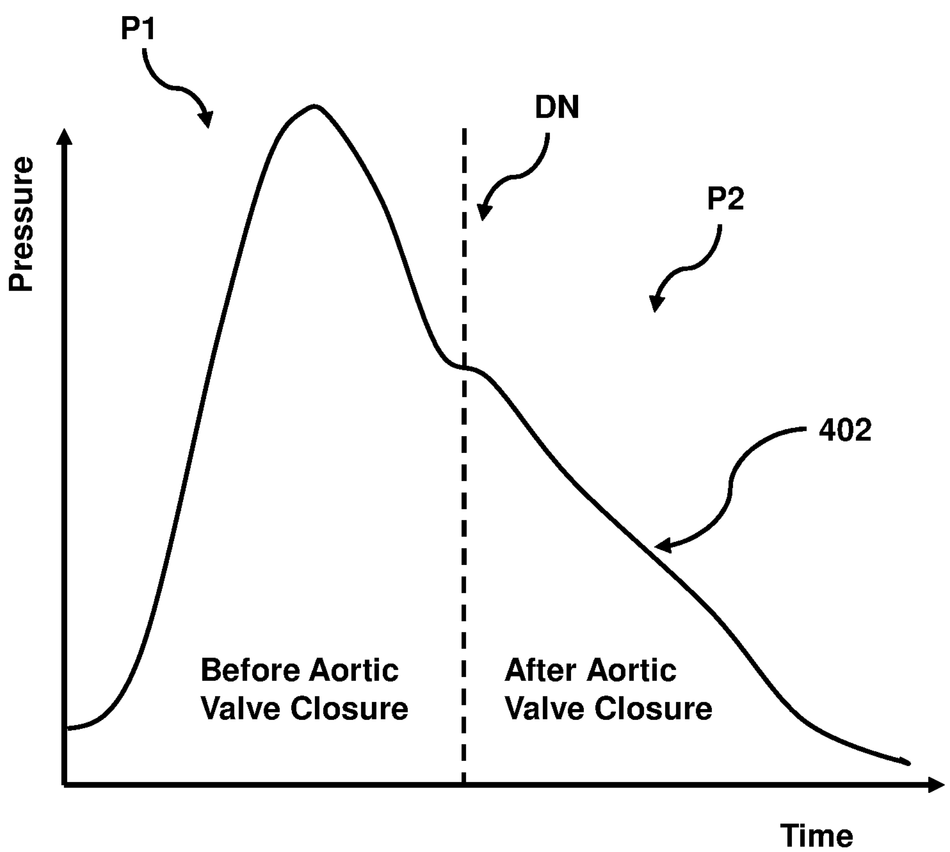

In some embodiments, cardiac parameter extraction module 316 may be configured to extract one or more cardiac parameters of the cardiac cycle of the patient based on the blood pressure waveform. The cardiac parameters may include, but are not limited to, which is not to imply that other lists are limiting, intrinsic frequencies, intrinsic phase angles, a relative height of dicrotic notch (RHDN), an envelope ratio (ER), an intrinsic envelope of systolic phase of the cardiac cycle, an intrinsic envelope of the diastolic phase of the cardiac cycle, or other cardiac parameters, or combinations thereof. In some cases, the left ventricle (LV) of the heart and aorta may be considered a coupled system before the aortic valve closes. The dicrotic notch indicates when the closure is beginning. The coupled system has a dominant frequency that the instantaneous frequency oscillates around. After the aortic valve closes, the heart and aorta are decoupled, and the dominate frequency is only based on the dynamics of the aorta and the arterial network. The dominate frequencies during systole and diastole, $\omega_1$ and $\omega_2$, are referred to as intrinsic frequencies. Additionally details regarding determining intrinsic frequencies are provided in "Intrinsic frequency for a systems approach to hemodynamic waveform analysis with clinical applications," Pahlevan et al., J. R. Soc. Interface 11: 20140617, the contents of which are incorporated herein by reference in their entireties. As seen in FIG. 4, for example, graph 400 includes a trace 402 of the blood pressure of a patient during a cardiac cycle. Trace 402 is segmented into two portions: P1 and P2. Portion P1 refers to the portion of the cardiac cycle before the aortic valve closes, and portion P2 refers to the portion of the cardiac cycle after the aortic valve closes. Portions P1 and P2 are separated by the dicrotic notch (DN).

The intrinsic frequencies $\omega_1$ and $\omega_2$ may be determined by modeling the aorta-heart coupled system as an object rotating around an origin. The angular velocity of the rotation is the intrinsic frequency. In the LV-arterial system, the average angular velocity during systole and diastole are the intrinsic frequencies (IFs) $\omega_1$ and $\omega_2$, respectively. The first IF, $\omega_1$, described the dynamics of the systolic phase of the cardiac cycle where the LV and the aorta form a coupled dynamic system. The second IF, $\omega_2$, is dominated by the dynamics of the vasculature of the decoupled system. To determine the IFs $\omega_1$ and $\omega_2$, Equation 2 may be solved:

$$\text{Minimize: } \|p(t) - \chi(0, T_0)[(a_1\cos(\omega_1 t) + b_1\sin(\omega_1 t) - \chi(T_0, T)[(a_2\cos(\omega_2 t) + b_2\sin(\omega_2 t) - c\|_2^2. \quad \text{Equation 2}$$

Equation 2 is an $L_2$ minimization subject to continuity at $T_0$ and periodicity of the waveform. In Equation 2, χ(a, b) is the indicator function (e.g., χ(a, b)=1 if a≤t≤b and χ(a, b)=0 otherwise), and p(t) is an arterial pressure waveform (e.g., ascending aorta, carotid, radial, etc.). Using trigonometric equations, the intrinsic frequency formulation can turn Equation 2 into Equation 3:

$$\text{Minimize: } \|p(t) - \chi(0, T_0)[(r_s\sin(\omega_1 t + \varphi_1)] - \chi(T_0, T)[(r_d\sin(\omega_2 t + \varphi_2)] - c\|_2^2. \quad \text{Equation 3}$$

Figure 5:
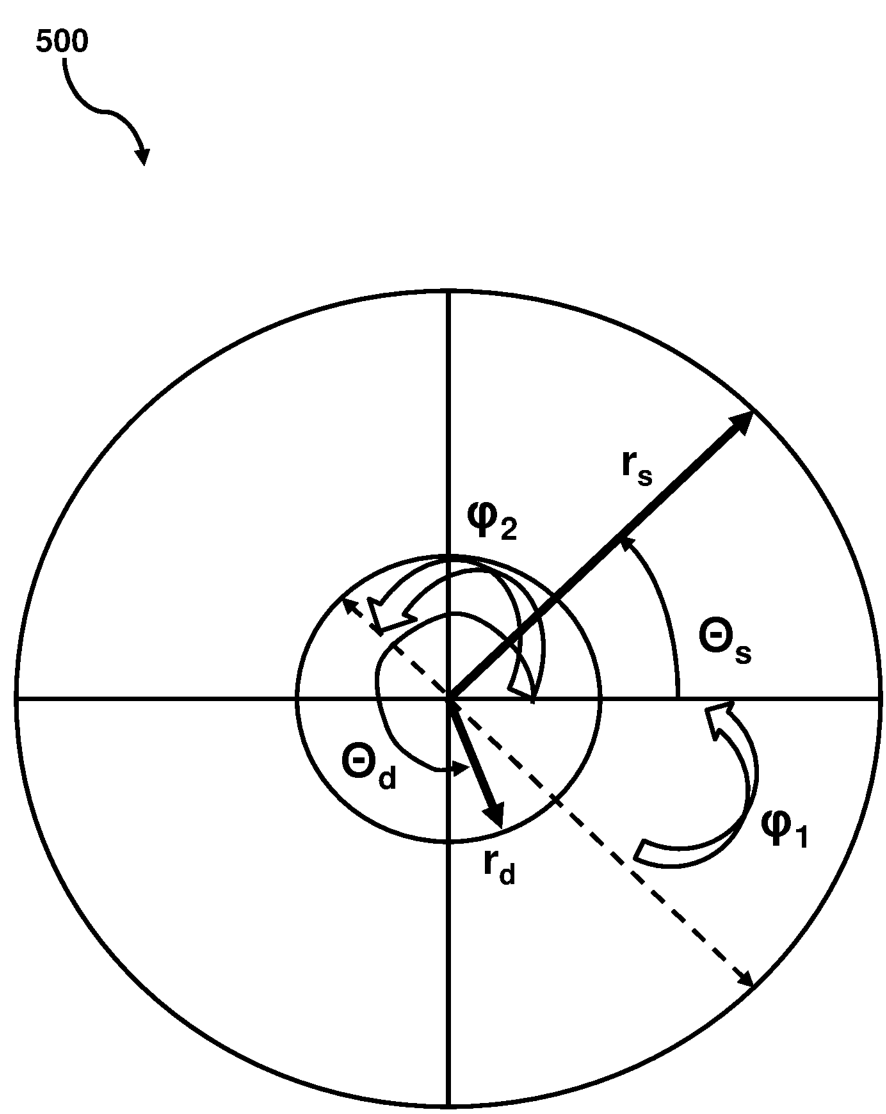
FIG. 5 illustrates an example visualization of intrinsic frequencies and intrinsic phase angles, in accordance with various embodiments.

In Equation 3, $\varphi_1$ and $\varphi_2$ are the systolic intrinsic phase angle and the diastolic intrinsic phase angle, respectively. A visual depiction of the relationship between the systolic intrinsic phase angle and the diastolic intrinsic phase angle to the intrinsic frequencies, $\omega_1$ and $\omega_2$ is seen in FIG. 5. In FIG. 5, visual depiction 500 describes the relationship between intrinsic frequencies $\omega_1$ and $\omega_2$, intrinsic phase angles, $\varphi_1$ and $\varphi_2$, the intrinsic envelope of systole, $r_s$, and the intrinsic envelope of diastole, $r_d$. The angles between the start of each cardiac phase (systolic or diastolic) and the reference angle line of zero (horizontal line toward right) are these intrinsic phase angles, $\varphi_1$ and $\varphi_2$. Equation 3 can be solved using brute-force method (similar to Equation 2), or using other optimization-based methods.

Returning to FIG. 3, cardiac parameter extraction module 316 may generate and output data 320 representing a set of cardiac parameters extracted from the cardiac pressure waveform. For example, output data 320 may include intrinsic frequencies $\omega_1$ and $\omega_2$, intrinsic phase angles, $\varphi_1$ and $\varphi_2$, the intrinsic envelope of systole, $r_s$, the intrinsic envelope of diastole, $r_d$, the RHDN, the ER, or other cardiac parameters.

Output data 320 may be stored in patient data database 136. In some embodiments, output data 320 may be stored in association with a pressure waveform, patient identifier, or other information.

Figure 6:
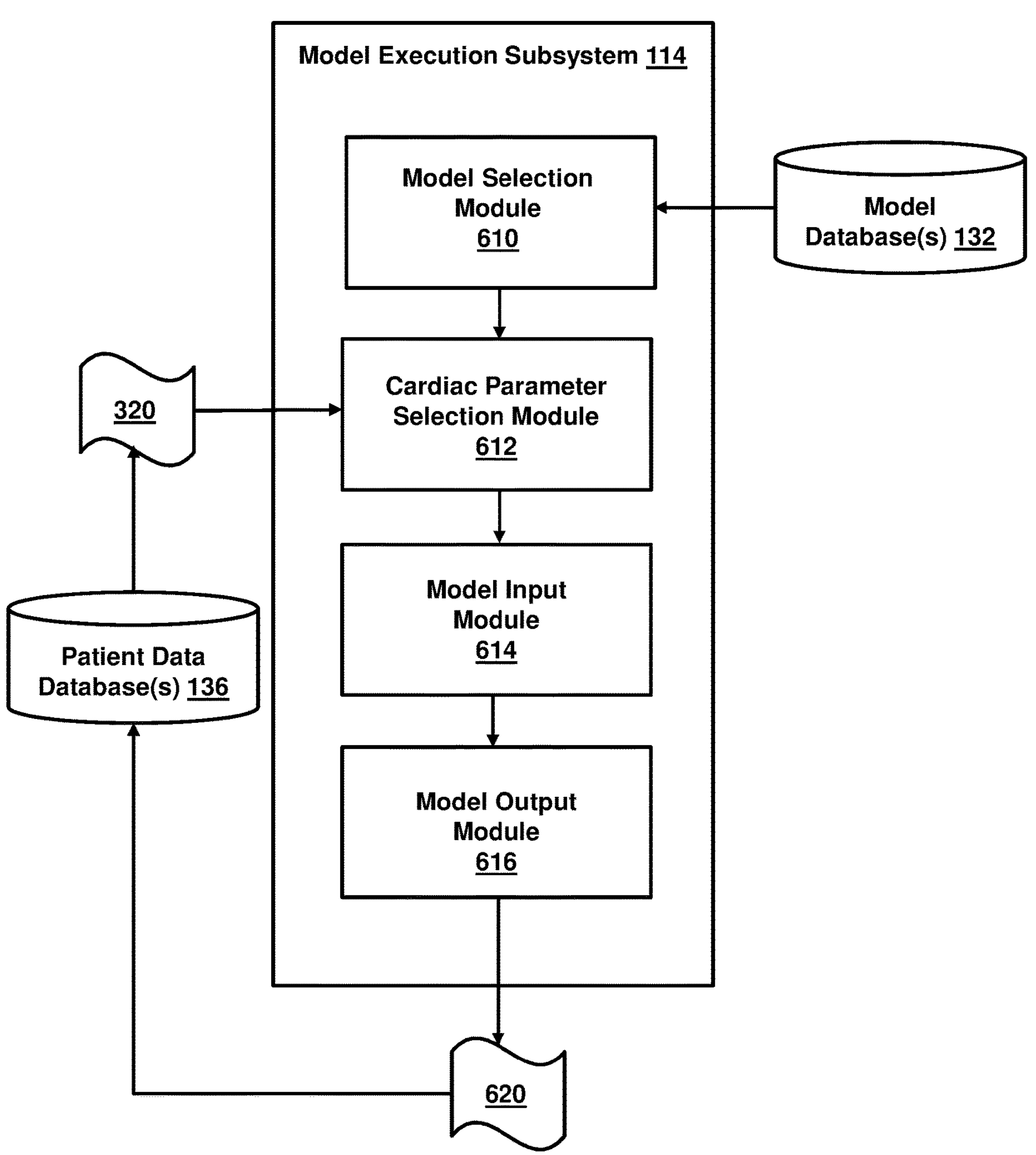
FIG. 6 illustrates an example model execution subsystem for executing a machine learning model for a given set of cardiac parameters, in accordance with various embodiments.

Returning to FIG. 1, model execution subsystem 114 may be configured to execute one or more machine learning models to determine various cardiac diagnoses. For instance, model execution subsystem 114 may execute a machine learning model trained to determine, based on an arterial pressure waveform, whether a patient has experienced one or more cardiac events (e.g., acute myocardial infarction, myocardial ischemia, etc.). Model execution subsystem 114 may also execute a machine learning model trained to determine, based on an arterial pressure waveform of a patient that experienced an MI, a size of that MI. As an example, with reference to FIG. 6, model execution subsystem 114 may include modules configured to execute tasks related to inputting output data 320 to a machine learning model and obtaining an output from the machine learning model, such as model selection module 610, cardiac parameter selection module 612, model input module 614, model output module 616, or other modules. Each of modules 610-616 may include software that executes certain tasks, and that software may be executed by one or more processors of the corresponding subsystem.

In some embodiments, model selection module 610 may select a machine learning model stored in model database 132 to be used to perform a particular task. Model selection module 610 may store various machine learning models, including trained machine learning models, which each may be trained to perform a particular analysis using output data 320. For example, model selection module 610 may select a trained machine learning model for determining whether a patient has experienced a cardiac event (e.g., an acute MI, myocardial ischemia, etc.). As another example, model selection module 610 may select a trained machine learning model for determining a size of a myocardial infarction experienced by a patient. In some embodiments, client device 104 may send a request to computing system 102 to perform a particular cardiac analysis for a patient, and the request may include an indication of a trained machine learning model to be selected, or criteria for selecting a trained machine learning model from the trained machine learning models stored within model database 132.

Cardiac parameter selection module 612 may obtain output data 320 including a set of cardiac parameters (e.g., computed from an arterial pressure waveform) of a patient's cardiac cycle. Depending on the type of analysis to be performed, and thus which trained machine learning model is to be executed, different input parameters may be needed. Cardiac parameter selection module 612 may select some or all of the set of cardiac parameters based on input requirements of the selected machine learning model. For instance, if the cardiac analysis to be performed is to determine whether a patient experienced one or more of a plurality of cardiac events (e.g., an acute MI, myocardial ischemia, etc.), cardiac parameter selection module 612 may select, from the set of cardiac parameters, a first intrinsic frequency $\omega_1$, a systolic intrinsic phase angle $\varphi_1$, $r_d$, $r_d$. or other cardiac parameters. Persons of ordinary skill in the art will recognize that output data 320 may include the cardiac parameters needed for a given cardiac analysis, and in some cases, a selection from extracted set of cardiac parameters may not be needed.

Figure 7A:
FIGS. 7A-7B are illustrative diagrams of example machine learning models for detecting cardiac events and determining a size of a myocardial infarction, respectively, in accordance with various embodiments.
Figure 7A:
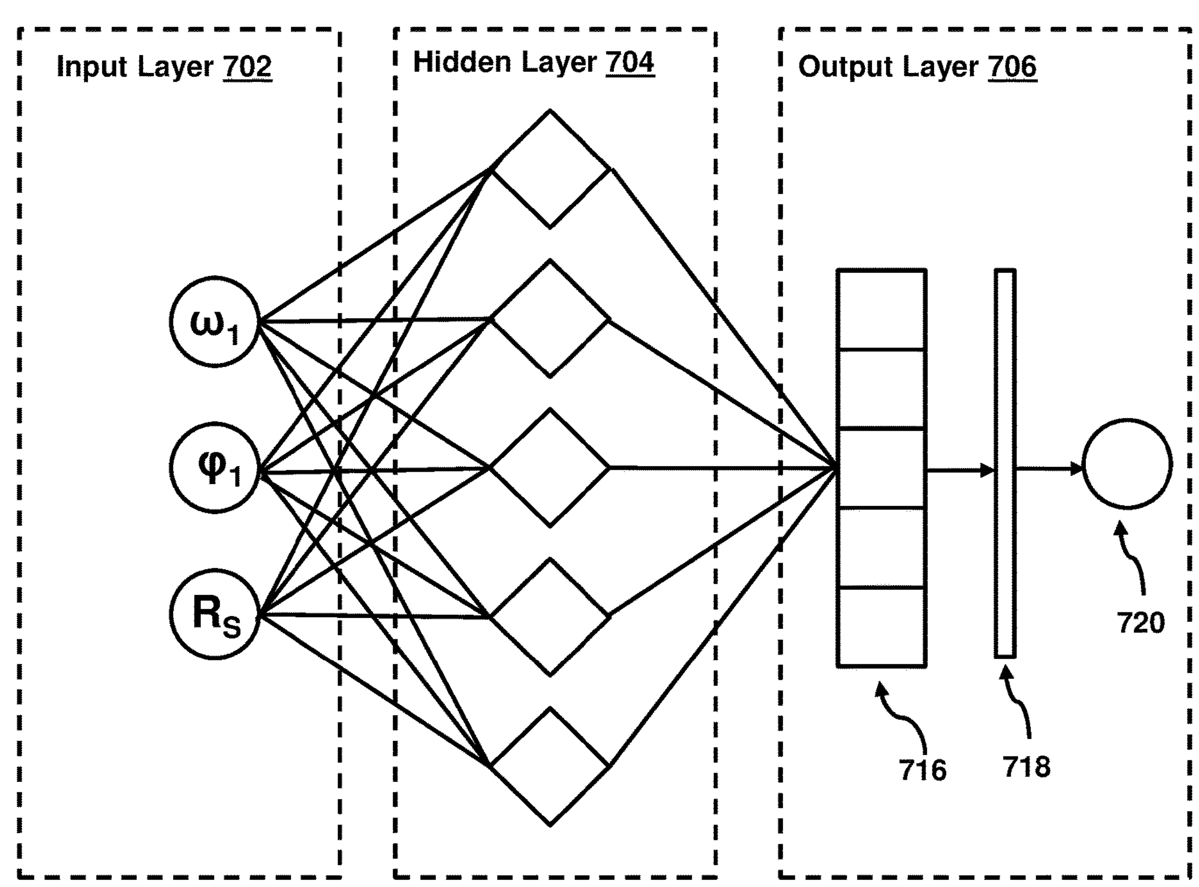
Figure 7B:
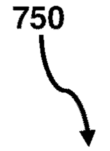
Figure 7B:
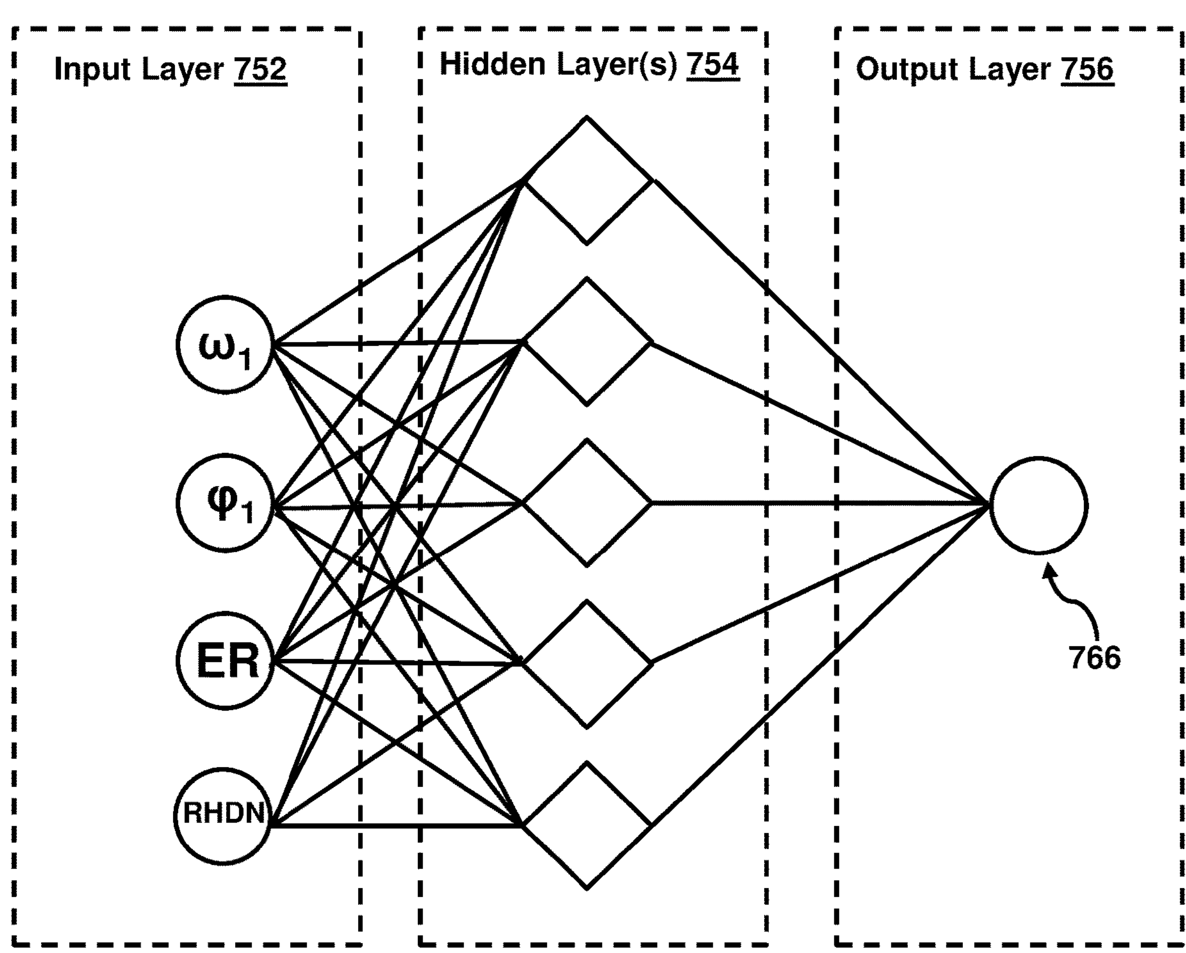

Model input module 614 may provide the selected cardiac parameters to the selected trained machine learning model, which may be configured to output a result 620 obtained by model output module 616. In some embodiments, the functionality of model input module 614 and model output module 616 may be combined into a single functional module. As an example, with reference to FIG. 7A, trained machine learning model 700 may be trained to determine whether a patient has experienced a cardiac event within a specified amount of time of the cardiac data being captured. As another example, with reference to FIG. 7B, trained machine learning model 750 may be trained to determine a size of a myocardial infarction experienced by a patient within a specified amount of time of the cardiac data being captured. The specified amount of time may differ between models 700 and 750, however they may also be the same or similar. Example amounts of times include within 24 hours of the MI, within 12 hours of the MI, within 2 hours of the MI, within 1 hour of the MI, or other amounts of time.

Trained machine learning models 700 and 750 may be any of the following types of machine learning models: Ordinary Least Squares Regression (OLSR), Linear Regression, Logistic Regression, Stepwise Regression, Multivariate Adaptive Regression Splines (MARS), Locally Estimated Scatterplot Smoothing (LOESS), Instance-based Algorithms, k-Nearest Neighbor (KNN), Learning Vector Quantization (LVQ), Self-Organizing Map (SOM), Locally Weighted Learning (LWL), Regularization Algorithms, Ridge Regression, Least Absolute Shrinkage and Selection Operator (LASSO), Elastic Net, Least-Angle Regression (LARS), Decision Tree Algorithms, Classification and Regression Tree (CART), Iterative Dichotomizer 3 (ID3), C4.5 and C5.0 (different versions of a powerful approach), Chi-squared Automatic Interaction Detection (CHAID), Decision Stump, M5, Conditional Decision Trees, Naive Bayes, Gaussian Naive Bayes, Causality Networks (CN), Multinomial Naive Bayes, Averaged One-Dependence Estimators (AODE), Bayesian Belief Network (BBN), Bayesian Network (BN), k-Means, k-Medians, K-cluster, Expectation Maximization (EM), Hierarchical Clustering, Association Rule Learning Algorithms, A-priori algorithm, Eclat algorithm, Artificial Neural Network Algorithms, Perceptron, Back-Propagation, Hopfield Network, Radial Basis Function Network (RBFN), Deep Learning Algorithms, Deep Boltzmann Machine (DBM), Deep Belief Networks (DBN), Convolutional Neural Network (CNN), Deep Metric Learning, Stacked Auto-Encoders, Dimensionality Reduction Algorithms, Principal Component Analysis (PCA), Principal Component Regression (PCR), Partial Least Squares Regression (PLSR), Collaborative Filtering (CF), Latent Affinity Matching (LAM), Cerebri Value Computation (CVC), Multidimensional Scaling (MDS), Projection Pursuit, Linear Discriminant Analysis (LDA), Mixture Discriminant Analysis (MDA), Quadratic Discriminant Analysis (QDA), Flexible Discriminant Analysis (FDA), Ensemble Algorithms, Boosting, Bootstrapped Aggregation (Bagging), AdaBoost, Stacked Generalization (blending), Gradient Boosting Machines (GBM), Gradient Boosted Regression Trees (GBRT), Random Forest, Computational intelligence (evolutionary algorithms, etc.), Computer Vision (CV), Natural Language Processing (NLP), Recommender Systems, Reinforcement Learning, Graphical Models, or separable convolutions (e.g., depth-separable convolutions, spatial separable convolutions, etc.).

Trained machine learning model 700 may include an input layer 702, one or more hidden layers 704, and an output layer 706. In some embodiments, input layer 702 includes three nodes, however additional or fewer nodes may be included. Each input node may receive one of a set of cardiac parameters capable if being used to determine whether a patient has recently experienced a cardiac event (e.g., such as an acute MI or myocardial ischemia). In some embodiments, trained machine learning model 700 may take, as input, a first intrinsic frequency $\omega_1$ associated with a systolic phase of a cardiac cycle, a systolic intrinsic phase angle $\varphi_1$, and an intrinsic envelope of systolic phase of the cardiac cycle. In some cases, an intrinsic envelope of the diastolic phase of the cardiac cycle may be used instead of the intrinsic envelope of systolic phase of the cardiac cycle. Furthermore, some cases may have a ratio of the intrinsic envelope of systolic phase of the cardiac cycle to the intrinsic envelope of the diastolic phase of the cardiac cycle.

Each node in input layer 702 may be fully connected to each node in hidden layer 704. However, for multiple hidden layers 704, some or all of the layers may be fully connected. Each node may include an activation function, such as a binary step function, a ReLU function, a Sigmoid function, a Softmax function, or other activation functions. In some cases, one or more of the nodes may include different activation functions. The outputs of hidden layers 704 may be provided to output layer 706.

In some embodiments, a classification vector 716 may be output from hidden layer 704. Classification vector 716 may be an n-dimensional classification vector, where each element includes a classification score representing a likelihood that the patient experienced one of n cardiac events. In some cases, trained machine learning model 700 may be trained such that it serves to detect whether a single type of cardiac event has occurred (e.g., whether the patient experienced an acute MI). In such cases, classification vector 716 may be a 1-dimensional vector, storing a classification score indicating how likely it is that the patient experienced an acute MI.

In some embodiments, output layer 706 may include a softmax layer 718 configured to take the outputs from the hidden layer(s) 704 and convert those classification scores to probabilities. Based on those probabilities, a determination may be made as to whether a given classification score satisfies a threshold condition. If so, then this indicates that the patient likely experienced a corresponding cardiac event. If not, then this may indicate that the patient did not experience from a corresponding cardiac event. In some embodiments, the threshold condition may be satisfied if the probability, or classification score, is greater than or equal to a threshold value. For example, if the probability that the patient experienced a certain cardiac event is greater than or equal to a threshold probability, then this indicates that the patient likely experienced the cardiac event, and thus may output result 720 indicating that the patient experienced the cardiac event, as well as, in some cases, the classification score, the probability, or both.

Trained machine learning model 750 may include an input layer 752, one or more hidden layers 754, and an output layer 756. In some embodiments, input layer 752 includes four nodes, however additional or fewer nodes may be included. Each input node may receive one of a set of cardiac parameters capable of being used to determine a size of an acute MI of a patient. In some embodiments, trained machine learning model 750 may take, as input, a first intrinsic frequency $\omega_1$ associated with a systolic phase of a cardiac cycle, a systolic intrinsic phase angle $\varphi_1$, an envelope ratio (ER) of the intrinsic envelope of the systolic phase to the diastolic phase, and a relative height of the dicrotic notch (RHDN).

Each node in input layer 752 may be fully connected to each node in hidden layer 754. However, for multiple hidden layers 754, some or all of the layers may be fully connected. Each node may include an activation function, such as a binary step function, a ReLU function, a Sigmoid function, a Softmax function, or other activation functions. In some cases, one or more of the nodes may include different activation functions. The outputs of hidden layers 754 may be provided to output layer 756.

In some embodiments, output layer 756 may output a result 766, which indicates an estimated size of the acute MI experienced by the patient. The estimated size may indicate an amount of carotid tissue that has become necrotic. In some embodiments, result 766 may be a numerical value between 0 and 1.0, a percentage, or other values.

Returning to FIG. 6, model output module 616 may obtain result 720 or result 766, depending on the model selected (e.g., trained machine learning model 700 or 750). Model output module 616 may generate output data including result 620, which may store result 720, 766 with the corresponding pressure waveform data, cardiac parameters, or other data for a particular patient. In some embodiments, patient data including result 720, 766, the pressure waveform data, cardiac parameters, and the like, for a patient may be stored in patient data database 136.

Figure 8:
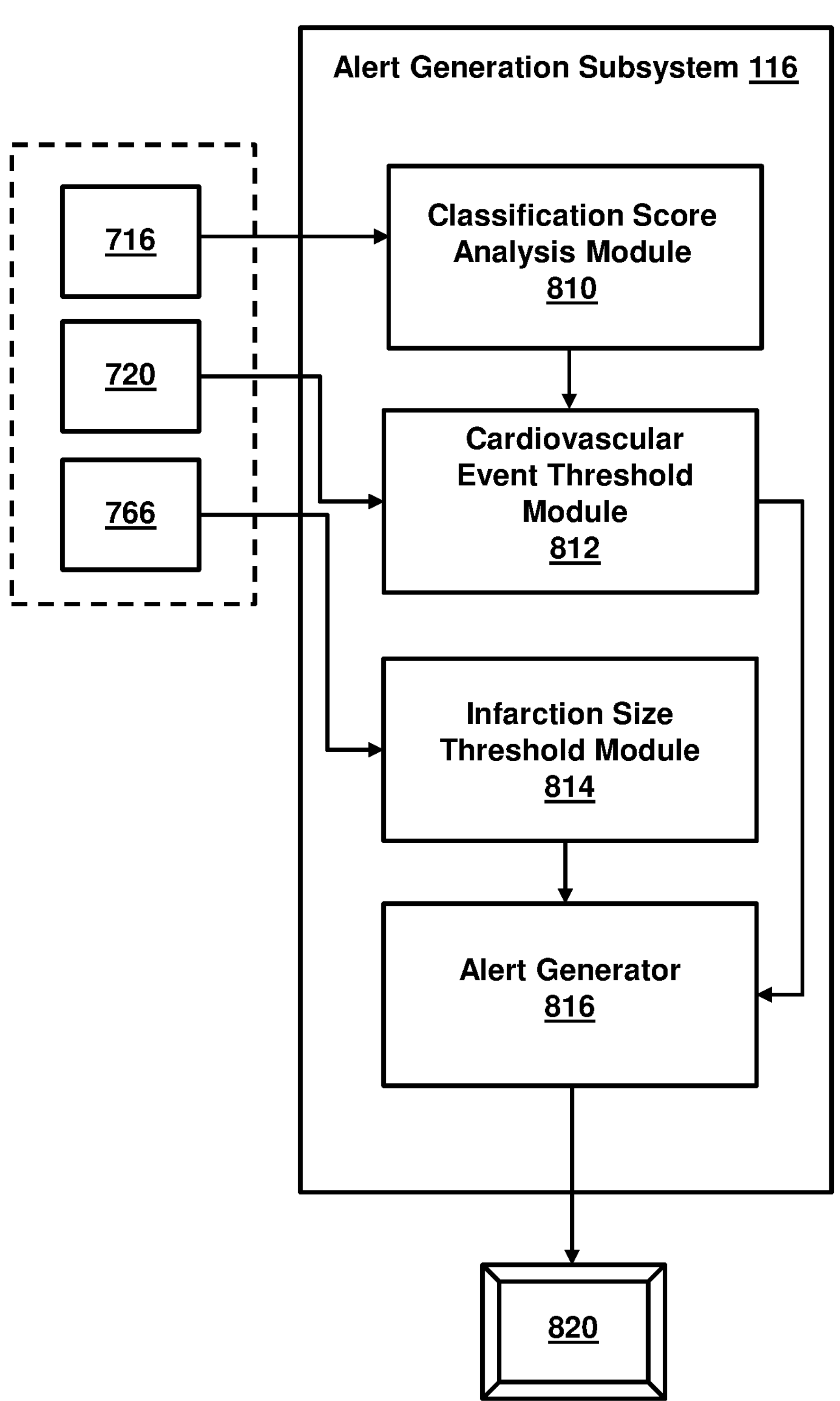
FIG. 8 illustrates an example alert generation subsystem for determining whether an alert should be generated regarding a patient's cardiac health, in accordance with various embodiments.

Returning to FIG. 1, alert generation subsystem 116 may be configured to determine whether an alert should be generated indicating result 720, 766, and other information about the patient's cardiac health. The alert may be provided to the patient, the patient's medical provider, or other entities. As an example, with reference to FIG. 8, alert generation subsystem 116 may include modules configured to execute tasks related to generating alerts regarding a patients cardiac health, as well as, or alternatively, determining whether the alert should be provided to the patient, the patient medical providers, other sources, or combinations thereof. The modules may include, for example, classification score analysis module 810, cardiovascular event threshold module 812, infarction size threshold module 814, alert generator 816, or other modules. Each of modules 810-816 may include software that executes certain tasks, and that software may be executed by one or more processors of the corresponding subsystem.

In some embodiments, classification score analysis module 810 may obtain classification vector 716 and determine a top N classification scores. The top N classification scores may be some or all of the classification scores determined by trained machine learning model 700. For example, a top classification score (e.g., for N=1), a top five classification scores (e.g., N=5), or other quantities of classification scores may be identified. In some embodiments, classification score analysis module 810 may apply a Softmax function to the classification scores to obtain a probability that the patient experienced one of the n possible cardiac events.

Cardiovascular event threshold module 812 may receive the top N classification scores, and may determine, for each classification score, whether that classification score satisfies a threshold condition. In some embodiments, the threshold condition may be satisfied when a given classification score is greater than or equal to a threshold classification score. For example, the threshold classification score may be 0.75, 0.80, 0.90, or other values. If the classification score satisfies the threshold condition, then that indicates that the patient experienced a corresponding cardiovascular event. For example, if the classification score associated with whether the patient experienced an acute MI is greater than a threshold classification score, specific to detection of acute MI or generalized for two or more cardiovascular events, then this indicates that trained machine learning model 700 determined that the patient likely experienced an acute MI (e.g., based on the cardiac parameters extracted from the patient's arterial pressure waveform). In some embodiments, cardiovascular event threshold module 812 may obtain result 720, indicating one or more cardiac events that the patient likely experienced. For instance, trained machine learning model 700 may determine, at output layer 706, a result indicating any cardiac events that the patient experienced based on the patient's arterial pressure waveform.

Alert generator 816 may obtain indications of which cardiac events the patients experienced, and may determine whether to generate an alert 820 to notify the patient, the patient's medical providers, or others, about the cardiac events experienced by the patient. In some embodiments, alert 820 may be generated whenever it has been determined that the patient experienced a cardiac event. Alert 820 may include a message, which may be textual, graphical, audible, or of another format, that is provided to the patient. Alert 820 may be provided to client devices 104 associated with the patient, the patient's medical providers, or others. In some embodiments, the message included by alert 820 may indicate that the patient experienced a particular cardiac event (or events). The message may also indicate that emergency assistance is needed for the patient, one or more therapies to be provided to the patient, or other information. Some cases include alert generator 816 contacting emergency services (e.g., automatically contacting police, emergency medical services, fire department, etc.).

Infarction size threshold module 814 may be configured to determine whether an infarct size, determined by trained machine learning model 750, satisfies a threshold infarction size condition. The threshold infarction size condition may be satisfied when an infarction size, indicated by result 766, is greater than or equal to a threshold infarction size. For example, if result 766 indicates that the infarction size is 20% (e.g., as a function of total heart tissue), and the threshold infarction size is 10%, then the infarction size can be said to satisfy the threshold infarction size condition. In some embodiments, alert generator 816 may be configured to generate and provide alert 820 to the patient, the patient's medical providers, or others, if the infarction size estimated by trained machine learning model 750 satisfies the threshold infarction size condition.

Returning to FIG. 1, model training subsystem 118 may be configured to train, re-train, update, reset, or perform other functions to obtain a trained machine learning model capable of being used as described herein. For instance, trained machine learning models 700 and 750 may be trained to determine whether a patient experienced a cardiovascular event and a size of a myocardial infarction experienced by a patient, respectively.

Figure 9:
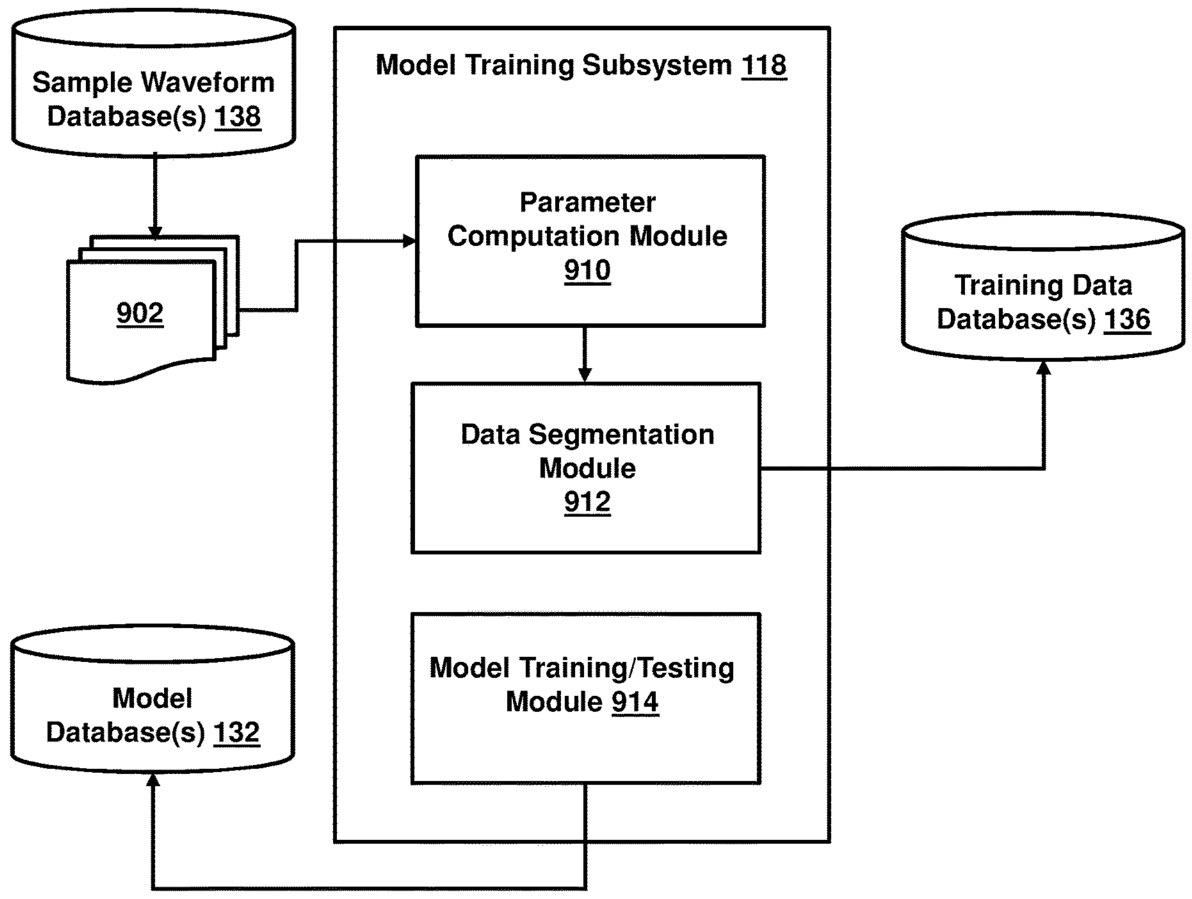
FIG. 9 illustrates an example model training subsystem for training and testing a machine learning model, in accordance with various embodiments.

With reference to FIG. 9, model training subsystem 118 may include a parameter computation module 910, a data segmentation module 912, a model training/testing module 914, or other modules. Each of modules 910-914 may include software that executes certain tasks, and that software may be executed by one or more processors of the corresponding subsystem.

Parameter computation module 910 may be configured to obtain datasets 902 from sample waveform database 138. Depending on the model to be trained (e.g., the function to be provided by the trained model), different datasets may be retrieved from sample waveform database 138. For example, if the model is to be trained to determine whether a patient experienced from one or more of a plurality of cardiovascular events, then datasets 902 may include a first set of waveforms (e.g., arterial pressure waveforms, pulse/heart rate waveforms, PIT waveforms, PPG waveforms, etc.) of patients who have experienced from one (or more) of the plurality of cardiovascular events, and a second set of waveforms of patients who have not experienced from the plurality of cardiovascular events. In some cases, each waveform included in datasets 902 may include metadata indicating a type of cardiac event experienced by a corresponding patient or metadata indicating that the patient has not experienced any cardiovascular events. Although the aforementioned example has datasets 902 including waveforms of a patient's arterial pressure/pulse-oxygen level, datasets 902 may, alternatively, include cardiac parameters extracted from each patient's waveform.

Parameter computation module 910 may be configured to compute one or more cardiac parameters from the waveforms included in datasets 902. For example, for each waveform (e.g., arterial pressure waveform, pulse-ox waveform, etc.), intrinsic frequencies $\omega_1$ and $\omega_2$, a systolic intrinsic phase angles $\varphi_1$ and $\varphi_2$, intrinsic envelopes $r_d$ and $r_s$, envelope ratio (ER), and a relative height of the dicrotic notch (RHDN), or other cardiac parameters. As detailed above, for a given arterial pressure waveform, an estimate of the cardiac parameters may be extracted using the intrinsic frequency (IF) method. In general, the IF method applies an adaptive sparse time-frequency representation (STFR) to an arterial pressure wave to extract the instantaneous frequency $$\left(\dot{\theta}_1(t) = \frac{d\theta_1}{dt}\right)$$

of the first intrinsic mode function (IMF; where $\theta_1$ is the phase angle of the first IMF) to determine a dominant instantaneous frequency on either side of the pressure waveform's dicrotic notch. To extract the intrinsic frequencies $\omega_1$ and $\omega_2$, the instantaneous frequency of the heart-aorta and decoupled aorta are taken to be piecewise constant in time. Doing so enables the intrinsic frequencies to be extracted from an arterial blood pressure waveform. The intrinsic frequencies are that carry the maximum power for Equation 4:

$$s(t) = \sum_{i=1}^{M} a_i(t)\cos\,\theta_i(t). \qquad \text{Equation 4}$$

To extract the intrinsic frequencies (IFs), a norm-2 ($L_2$) minimization technique. The envelopes of the IMF may also be piecewise constant in time. The $L_2$ minimization problem may then be represented by Equation 5:

$$\text{min: } \|f(t) - \chi(0, T_0)s_1(t) - \chi(T_0, T)s_2(t) - c\|_2^2. \qquad \text{Equation 5}$$

Equation 5 is subject to the following constraints:

$$a_1\cos(\omega_1 T_0) + b_1\sin(\omega_1 T) = a_2\cos(\omega_2 T_0) + b_2\sin(\omega_2 T_0)a_1 = a_2\cos(\omega_2 T) + b_1\sin(\omega_2 T)s_1(t) = a_1\cos(\omega_1 t) + b_1\sin(\omega_1 t)s_2(t) = a_2\cos(\omega_2 t) + b_2\sin(\omega_2 t)\chi(a, b) = \begin{cases} 1 & a \le t \le b \\ 0 & \text{otherwise} \end{cases}; \qquad \text{Equation 6}$$

$$a_1\cos(\omega_1 T_0) + b_1\sin(\omega_1 T) = a_2\cos(\omega_2 T_0) + b_2\sin(\omega_2 T_0)a_1 = a_2\cos(\omega_2 T) + b_1\sin(\omega_2 T)s_1(t) = a_1\cos(\omega_1 t) + b_1\sin(\omega_1 t)s_2(t) = \qquad \text{Equation 7}$$

-continued $$a_2\cos(\omega_2 t) + b_2\sin(\omega_2 t)\chi(a, b) = \begin{cases} 1 & a \le t \le b \\ 0 & \text{otherwise} \end{cases};$$

Equation 8

$$a_1\cos(\omega_1 T_0) + b_1\sin(\omega_1 T) = a_2\cos(\omega_2 T_0) + b_2\sin(\omega_2 T_0)a_1 = a_2\cos(\omega_2 T) + b_1\sin(\omega_2 T)s_1(t) = a_1\cos(\omega_1 t) + b_1\sin(\omega_1 t)s_2(t) = a_2\cos(\omega_2 t) + b_2\sin(\omega_2 t)\chi(a, b) = \begin{cases} 1 & a \le t \le b \\ 0 & \text{otherwise} \end{cases};$$

Equation 9

$$a_1\cos(\omega_1 T_0) + b_1\sin(\omega_1 T) = a_2\cos(\omega_2 T_0) + b_2\sin(\omega_2 T_0)a_1 = a_2\cos(\omega_2 T) + b_1\sin(\omega_2 T)s_1(t) = a_1\cos(\omega_1 t) + b_1\sin(\omega_1 t)s_2(t) = a_2\cos(\omega_2 t) + b_2\sin(\omega_2 t)\chi(a, b) = \begin{cases} 1 & a \le t \le b \\ 0 & \text{otherwise} \end{cases};$$

Equation 10

$$a_1\cos(\omega_1 T_0) + b_1\sin(\omega_1 T) = a_2\cos(\omega_2 T_0) + b_2\sin(\omega_2 T_0)a_1 = a_2\cos(\omega_2 T) + b_1\sin(\omega_2 T)s_1(t) = a_1\cos(\omega_1 t) + b_1\sin(\omega_1 t)s_2(t) = a_2\cos(\omega_2 t) + b_2\sin(\omega_2 t)\chi(a, b) = \begin{cases} 1 & a \le t \le b \\ 0 & \text{otherwise} \end{cases}.$$

Additionally, in Equation 5, c is a constant. Thus, based on Equations 6-10, Equation 5 may be transformed into solving for $a_1$, $a_2$, c, $b_1$, $b_2$, $\omega_1$, and $\omega_2$. Time $T_0$ refers to the time of the dicrotic notch in the pressure wave. The minimization states that the aortic input pressure wave can be approximated by two incomplete sinusoids with different frequencies, the intrinsic frequencies $\omega_1$, and $\omega_2$, where $\omega_1$ is the intrinsic frequency for the heart+aorta system (e.g., before aortic valve closure=before the dicrotic notch), and $\omega_2$ is the intrinsic frequency for the decoupled aorta (e.g., after aortic valve closure=after dicrotic notch). Using trigonometric identifies, Equation 5 can be transformed into Equation 11:

Equation 11

$$\min: \|p(t) - \chi(0, T_0)[r_s\sin(\omega_1 t + \varphi_1)] - \chi(T_0, T)[r_d\sin(\omega_2 t + \varphi_2)] - c\|_2^2.$$

From Equation 11, the cardiac parameters $\omega_1$, $\omega_2$, $\omega_1$, $\omega_2$, $r_d$, $r_s$, ER, RHDN, or other parameters, may be extracted.

Data segmentation module 912 may obtain a set of cardiac parameters for each waveform of a first plurality of waveforms respectively corresponding to a first plurality of patients that have experienced from one or more of a plurality of cardiac events (e.g., acute MI, myocardial ischemia, etc.) and may obtain a set of cardiac parameters for each waveform of a second plurality of waveform, respectively corresponding to a second plurality of patients that have not experienced from any of the plurality of cardiac events (e.g., patients that have not experienced an acute MI). In some embodiments, waveform data may be updated to include the cardiac parameters, such that, for each waveform of the first and second pluralities of waveforms, the waveform data indicates each of the cardiac parameters computed for a given waveform and, if available, a label indicating a type of cardiac event that was experienced for a given patient. The waveform data may be provided to training data database 134 as training data, which will be used to train a machine learning model (e.g., trained machine learning model 700). In some embodiments, waveforms of the first plurality of waveforms that correspond to acute MIs may be selected for training of a machine learning model (e.g., trained machine learning model 750) to estimate an infarct size of the acute MI. Thus, for some or all of the selected waveforms (e.g., waveforms of patients that have experienced acute MI), a value indicating an infarct size determined using traditional techniques (e.g., ECGs, MRIs, computed tomography (CT) scans, single photon emission computed tomography (SPECT) scans, or other techniques.

In some embodiments, data segmentation module 812 may segment the cardiac data (e.g., waveforms, cardiac parameters, labels, values, etc.) into training data and testing data. The training data may be used to train machine learning model 700, machine learning model 750, or both, however, different training data may be generated for each machine learning model. In some embodiments, one or more cardiac parameters, labels, values, or other data may be masked when stored. For example, a label indicating a type of cardiac event that a patient experienced may be masked in the training data, and may be unmasked for the testing data. As another example, a size of the infarct may be masked in the training data and may be unmasked in the testing data.

Figure 10:
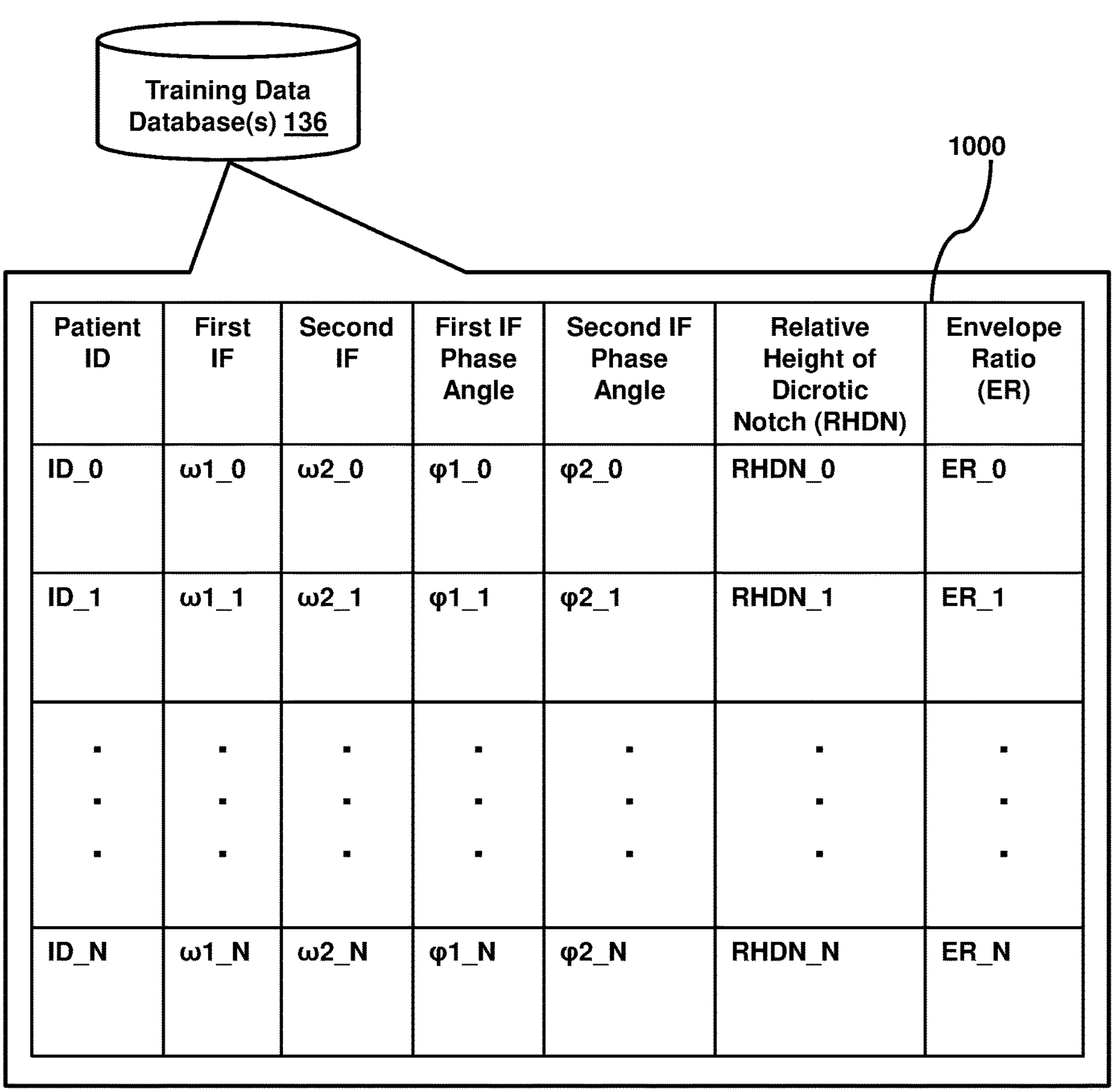
FIG. 10 is an example of a data structure used to store cardiac parameters included within training data for training a machine learning model, in accordance with various embodiments.

FIG. 10 is an example of a data structure 1000 used to store cardiac parameters included within training data for training a machine learning model, in accordance with various embodiments. Data structure 1000 includes N entries, each corresponding to a particular patient, indicating by patient identifiers ID_0-ID_N. In some cases, a given patient may have multiple entries, and so N may corresponding to a number of different pressure waveforms of the patient IDs_0-ID_N. However, for simplicity, data structure 1000 includes N entries corresponding to N patients, where each patient has a single pressure waveform computed. In some embodiments, various cardiac parameters may be extracted/computed from that patient's pressure waveform based on the IF method, detailed above. (Alternatively different approaches may be used to compute certain cardiac parameters, and the concepts described herein are not limited to only those techniques.) For example, for each entry, and thus each patient (e.g., ID_0-ID_N), data structure 1000 may store intrinsic frequencies $\omega_1$ and $\omega_2$, systolic intrinsic phase angles $\varphi_1$ and diastolic intrinsic phase angle $\varphi_2$, intrinsic envelopes $r_d$ and $r_s$, envelope ratio (ER), and a relative height of the dicrotic notch (RHDN), or other cardiac parameters.

Returning to FIG. 9, model training/testing module 914 may be configured to train and test a given machine learning model using the training data and testing data stored within training data database 134. In some embodiments, model training/testing module 914 may execute one or more optimization techniques, such as gradient descent, to minimize an error of each machine learning model until the model's accuracy is determined to reach some threshold criteria (e.g., 75% or greater accuracy, 80% or greater accuracy, 90% or greater accuracy, or other accuracy values). After the threshold criteria is met, the trained machine learning model (e.g., trained machine learning models 700, 750) may be stored in model database 132. In some cases, some or all machine learning models, training data, or both, may be retrained, updated, or both. The updating and/or the retraining may occur periodically, such as daily, weekly, monthly, etc. In some cases, the updating/retraining may be performed in response to a request to have the training data updated or a model be retrained. In some embodiments, the updating/retraining may occur in response to determining that a model fails to produce accurate results (e.g., its accuracy falls below a threshold accuracy).

The various machine learning models stored by model database 132, trained and/or untrained, include, but are not limited to (which is not to suggest that any other list is limiting), any of the following: Ordinary Least Squares Regression (OLSR), Linear Regression, Logistic Regression, Stepwise Regression, Multivariate Adaptive Regression Splines (MARS), Locally Estimated Scatterplot Smoothing (LOESS), Instance-based Algorithms, k-Nearest Neighbor (KNN), Learning Vector Quantization (LVQ), Self-Organizing Map (SOM), Locally Weighted Learning (LWL), Regularization Algorithms, Ridge Regression, Least Absolute Shrinkage and Selection Operator (LASSO), Elastic Net, Least-Angle Regression (LARS), Decision Tree Algorithms, Classification and Regression Tree (CART), Iterative Dichotomizer 3 (ID3), C4.5 and C5.0 (different versions of a powerful approach), Chi-squared Automatic Interaction Detection (CHAID), Decision Stump, M5, Conditional Decision Trees, Naive Bayes, Gaussian Naive Bayes, Causality Networks (CN), Multinomial Naive Bayes, Averaged One-Dependence Estimators (AODE), Bayesian Belief Network (BBN), Bayesian Network (BN), k-Means, k-Medians, K-cluster, Expectation Maximization (EM), Hierarchical Clustering, Association Rule Learning Algorithms, A-priori algorithm, Eclat algorithm, Artificial Neural Network Algorithms, Perceptron, Back-Propagation, Hopfield Network, Radial Basis Function Network (RBFN), Deep Learning Algorithms, Deep Boltzmann Machine (DBM), Deep Belief Networks (DBN), Convolutional Neural Network (CNN), Deep Metric Learning, Stacked Auto-Encoders, Dimensionality Reduction Algorithms, Principal Component Analysis (PCA), Principal Component Regression (PCR), Partial Least Squares Regression (PLSR), Collaborative Filtering (CF), Latent Affinity Matching (LAM), Cerebri Value Computation (CVC), Multidimensional Scaling (MDS), Projection Pursuit, Linear Discriminant Analysis (LDA), Mixture Discriminant Analysis (MDA), Quadratic Discriminant Analysis (QDA), Flexible Discriminant Analysis (FDA), Ensemble Algorithms, Boosting, Bootstrapped Aggregation (Bagging), AdaBoost, Stacked Generalization (blending), Gradient Boosting Machines (GBM), Gradient Boosted Regression Trees (GBRT), Random Forest, Computational intelligence (evolutionary algorithms, etc.), Computer Vision (CV), Natural Language Processing (NLP), Recommender Systems, Reinforcement Learning, Graphical Models, or separable convolutions (e.g., depth-separable convolutions, spatial separable convolutions, etc.).

Example Flowcharts

FIGS. 11A-14 are example flowcharts of processing operations of methods that enable the various features and functionality of the system as described in detail above. The processing operations of each method presented below are intended to be illustrative and non-limiting. In some embodiments, for example, the methods may be accomplished with one or more additional operations not described, and/or without one or more of the operations discussed. Additionally, the order in which the processing operations of the methods are illustrated (and described below) is not intended to be limiting.

In some embodiments, the methods may be implemented in one or more processing devices (e.g., a digital processor, an analog processor, a digital circuit designed to process information, an analog circuit designed to process information, a state machine, and/or other mechanisms for electronically processing information). The processing devices may include one or more devices executing some or all of the operations of the methods in response to instructions stored electronically on an electronic storage medium. The processing devices may include one or more devices configured through hardware, firmware, and/or software to be specifically designed for execution of one or more of the operations of the methods.

Figure 11A:
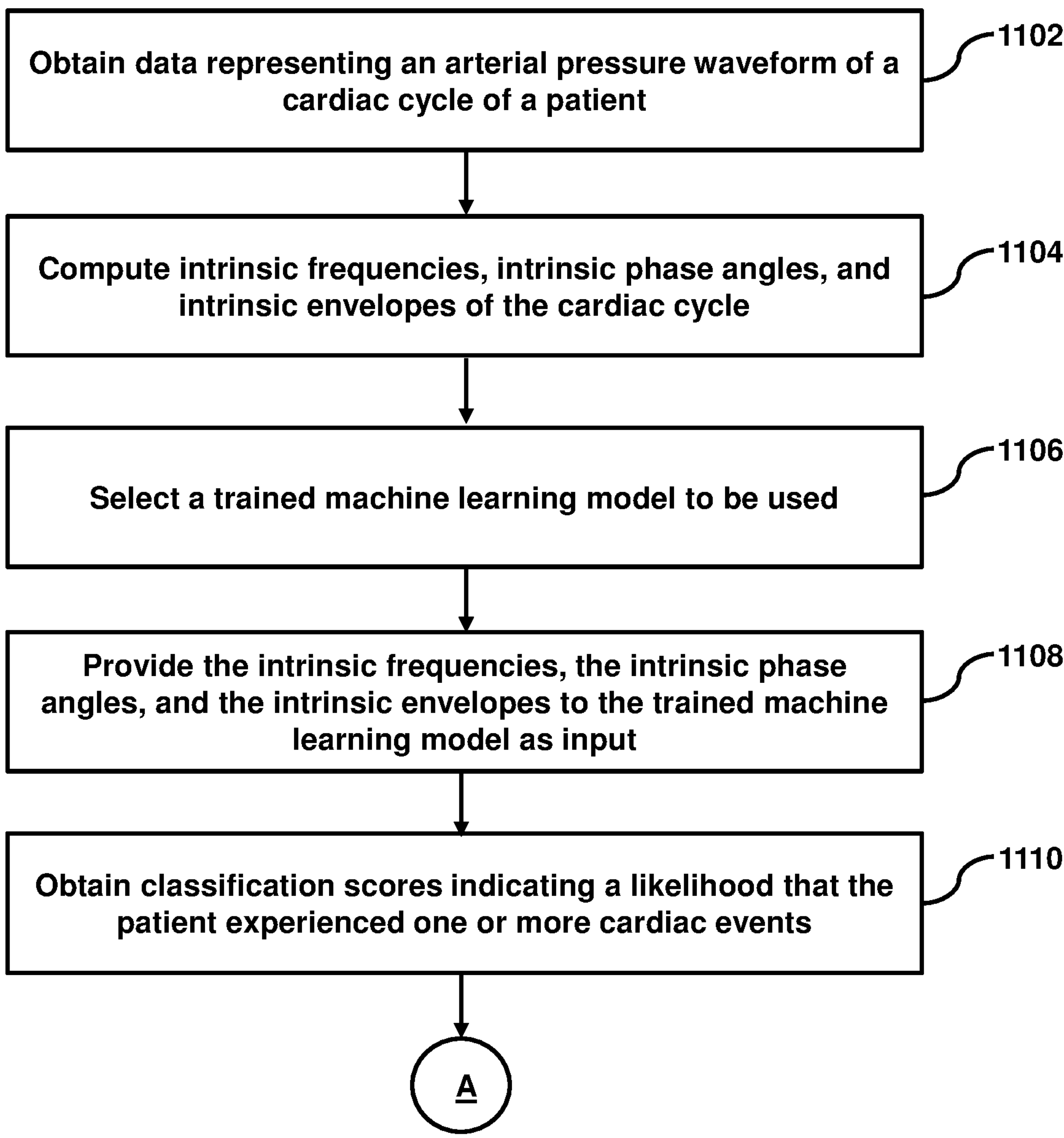
FIGS. 11A-11B illustrate an example process for using a machine learning model to determine whether a patient has experienced a cardiac event or a determining a size of a myocardial infarction experienced by a patient, in accordance with various embodiments.
Figure 11B:
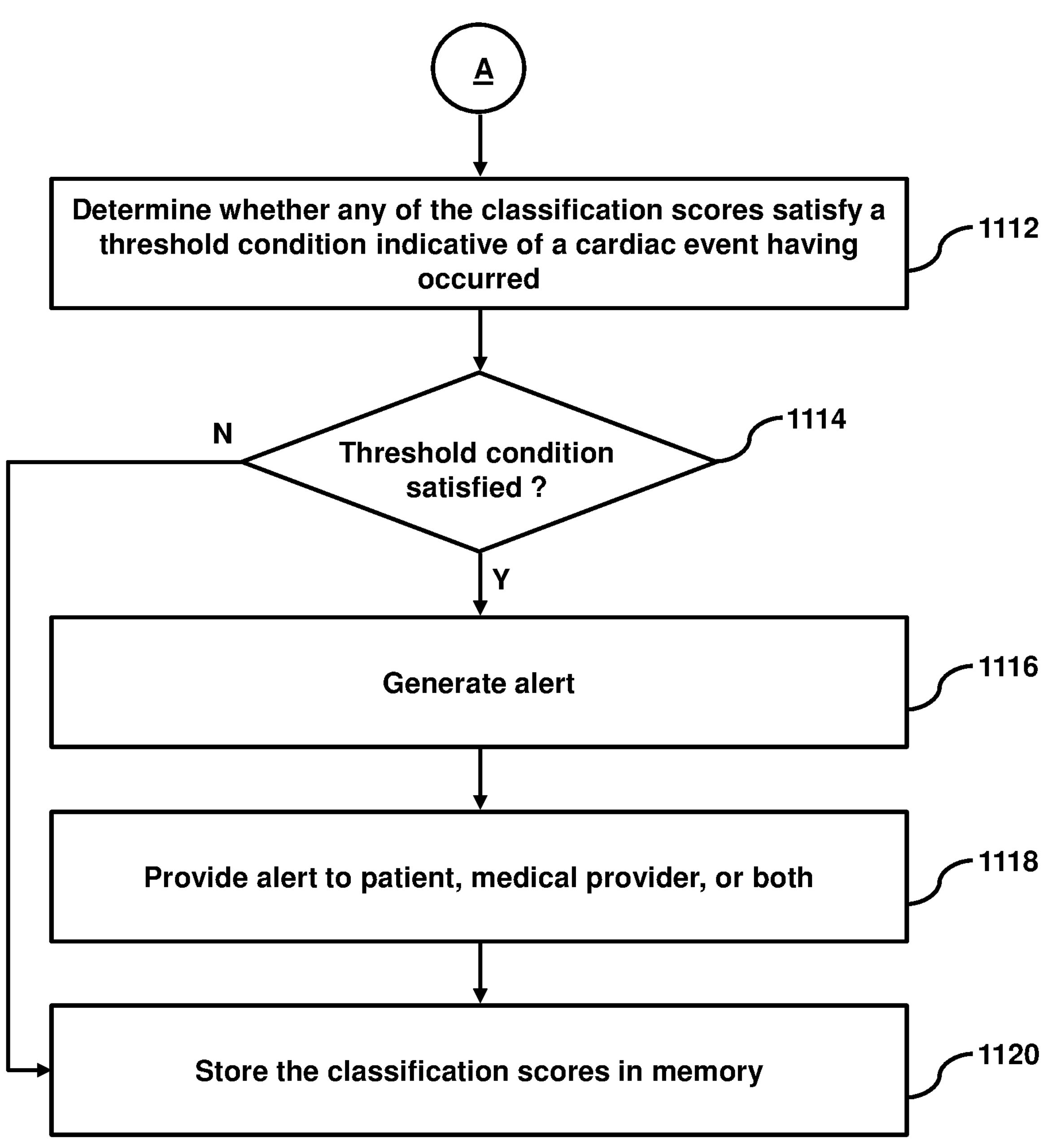

FIGS. 11A-11B illustrate an example process for using a machine learning model to determine whether a patient has experienced a cardiac event or a determining a size of a myocardial infarction experienced by a patient, in accordance with various embodiments. In some embodiments, process 1100 may begin at operation 1102. In operation 1102, data representing an arterial pressure waveform of a cardiac cycle of a patient may be obtained. The arterial pressure waveform may constructed based on measurements captured by client device 104 (e.g., a wearable device, via a smartphone's camera, etc.). The measurements may capture the patient's heart rate, PTT, blood pressure, or other physiological health metrics. In some embodiments, the data may include PPG signals/waveforms, ECG signals/waveforms, or other data. In some embodiments, operation 1102 may be performed by a subsystem that is the same or similar to cardiovascular parameter subsystem 112.

In operation 1104, intrinsic frequencies, intrinsic phase angles, intrinsic envelopes, and other features of the cardiac cycle of the patient may be computed. For example, based on a given pressure waveform, intrinsic frequencies $\omega_1$ and $\omega_2$, systolic intrinsic phase angles $\varphi_1$ and diastolic intrinsic phase angle $\varphi_2$, intrinsic envelopes $r_d$ and $r_s$, envelope ratio (ER), and a relative height of the dicrotic notch (RHDN), or other cardiac parameters may be computed. In some embodiments, the IF method described above, with reference to "Noninvasive iPhone Measurement of Left Ventricular Ejection Fraction Using Intrinsic Frequency Methodology," Pahlevan et al., Critical Care Medicine, 2017; 45:1115-1120, the contents of which is hereby incorporated by reference in its entirety, may be used to determine the aforementioned cardiac parameters. The cardiac parameters computed may be based on a type of analysis to be performed by a given machine learning model. Therefore, some or all of the possible cardiac parameters may be computed. In some embodiments, operation 1104 may be performed by a subsystem that is the same or similar to cardiovascular parameter subsystem 112.

In operation 1106, a trained machine learning model to be used to perform a particular analysis may be selected. For instance, model database 132 may store a plurality of trained machine learning models (as well as untrained machine learning models), each capable of performing one or more specific prediction tasks. Depending on the type of analysis to be done, different machine learning models may be selected. Additionally, depending on the specific cardiac parameters that are available, different machine learning models may be selected. As an example, trained machine learning model 700 may be selected if the analysis is to be a determination, using noninvasive techniques (e.g., such as via the IF method) one or more cardiac events occurred based on an arterial pressure waveform of a cardiac cycle of a patient. As another example, training machine learning model 750 may be selected if the analysis to be performed, using noninvasive techniques (e.g., such as via the IF method), is determining a size of an infarction. In some embodiments, operation 1106 may be performed by a subsystem that is the same or similar to model execution subsystem 114.

In operation 1108, the intrinsic frequencies, intrinsic phase angles, and the intrinsic envelopes may be provided, as input, to the trained machine learning model that was selected. For example, a first IF $\omega_1$, a systolic intrinsic phase angles $\varphi_1$, and intrinsic envelope $r_d$ and/or $r_s$ may be provided to trained machine learning model 700 as input. In operation 1110, classification scores indicating a likelihood that the patient experienced one or more cardiac events may be obtained. Each classification score may indicate a likelihood that a corresponding cardiac event occurred. For example, a first classification score may indicate whether the patient experienced an acute MI. In some embodiments, operations 1108 and 1110 may be performed by a subsystem that is the same or similar to model execution subsystem 114.

At operation 1112, a determination may be made as to whether any of the classification scores satisfy a threshold condition indicative of a cardiac event having occurred based on the input cardiac parameters derived from the arterial pressure waveform of the patient. In some embodiments, the threshold condition may be satisfied when a classification score is greater than or equal to a threshold classification score. The threshold classification score may be specific to a particular cardiac event or may be generalized for some or all of the classification scores. In some embodiments, operation 1112 may be performed by a subsystem that is the same or similar to alert generation subsystem 116.

At operation 1114, it is determined whether the threshold condition was satisfied. If so, then process 1100 may proceed to operation 1116, where an alert is generated, or, if not, process 1100 may proceed to operation 1120, where the classification scores are stored in memory. In some embodiments, the alert may be a message, such as a text message, video message, image, or other message. In operation 1118, the generated alert may be provided to the patient, the patient's medical provider, or both, depending on the preferences of the patient and health privacy rules. In some embodiments, operations 1114-1120 may be performed by a subsystem that is the same or similar to alert generation subsystem 116.

Figure 12A:
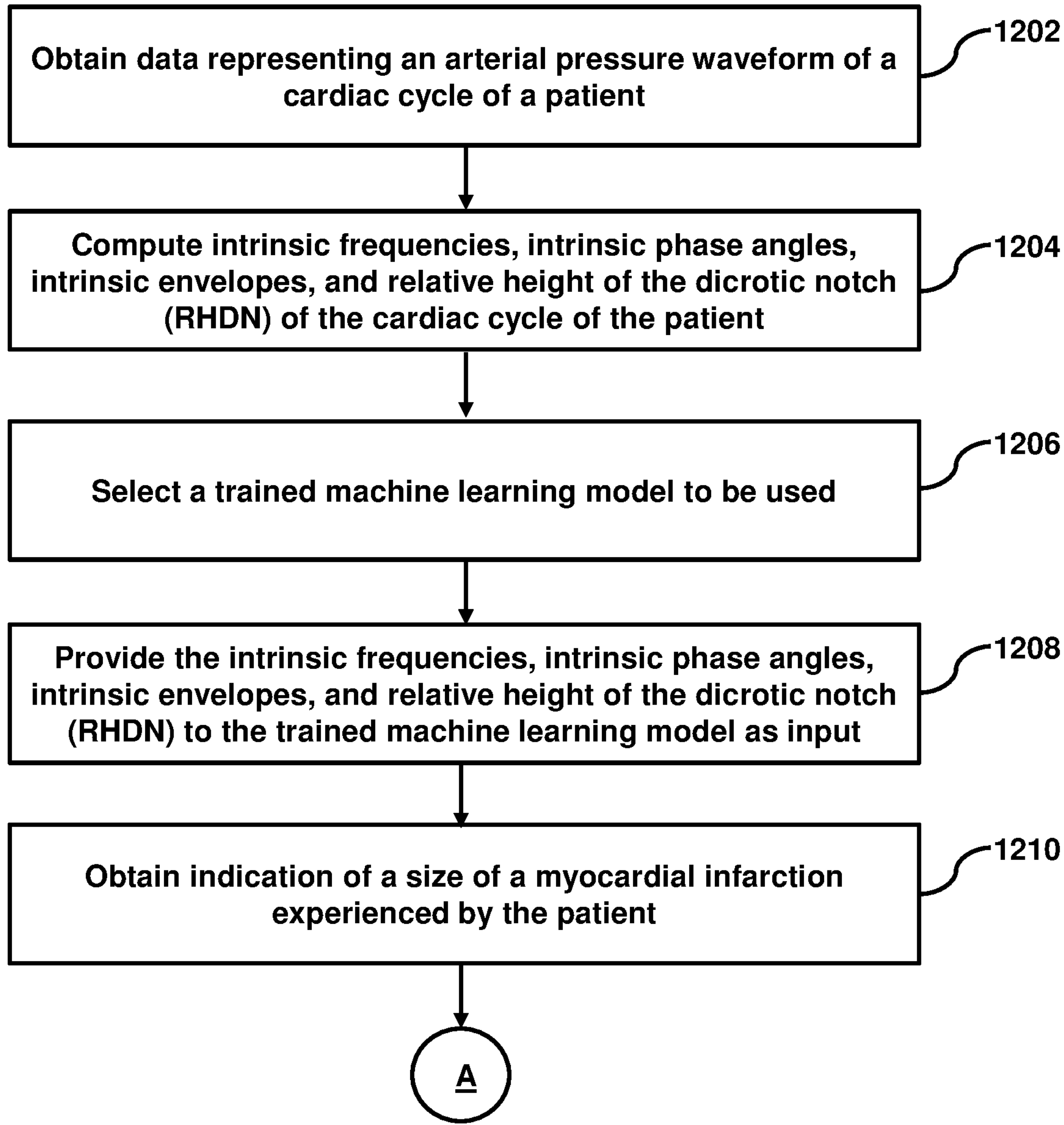
FIGS. 12A-12B illustrate an example process for using a machine learning model to determine a size of a myocardial infarction experienced by a patient, in accordance with various embodiments.
Figure 12B:
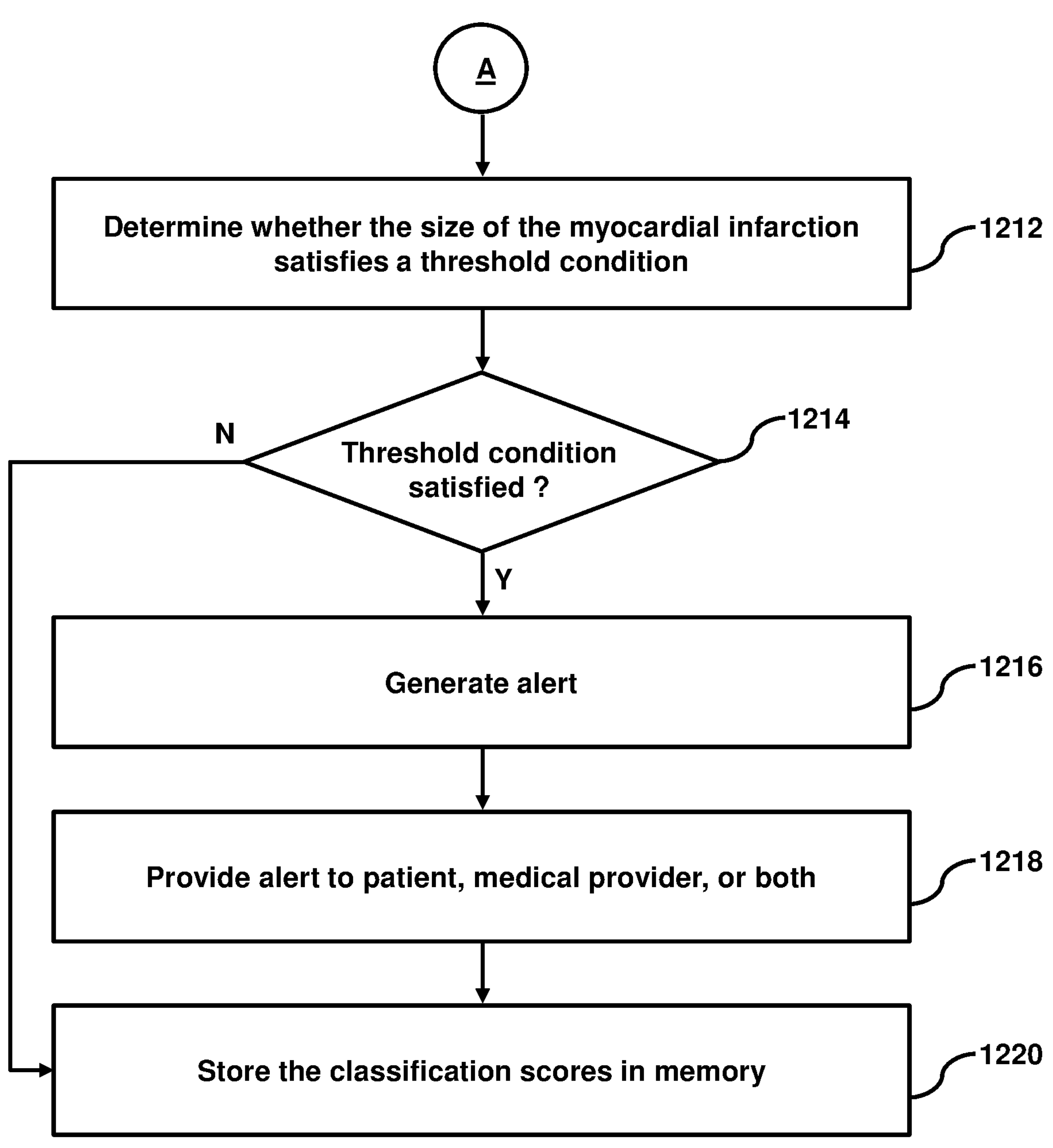

FIGS. 12A-12B illustrate an example process for using a machine learning model to determine a size of a myocardial infarction experienced by a patient, in accordance with various embodiments. In some embodiments, process 1200 may begin at operation 1202. In operation 1202, data representing an arterial pressure waveform of a cardiac cycle of a patient may be obtained. In some embodiments, the data obtained in operation 1202 may be substantially similar to the data obtained at operation 1102, with the exception that the cardiac cycles of the patient associated with the data captured in operation 1202 may be for patients who have recently experienced a particular cardiac event, such as an acute MI. In operation 1204, intrinsic frequencies, intrinsic phase angles, intrinsic envelopes, relative height of the dicrotic notch, envelope ratio, or other cardiac parameters, may be computed from the data. Operation 1204 may be substantially similar to operation 1104, and the previous description may apply.

In operation 1206, a trained machine learning model may be selected. For instance, model database 132 may store a plurality of trained machine learning models (as well as untrained machine learning models), each capable of performing one or more specific prediction tasks. Depending on the type of analysis to be done, different machine learning models may be selected. Additionally, depending on the specific cardiac parameters that are available, different machine learning models may be selected. As an example, trained machine learning model 700 may be selected if the analysis is to be a determination, using noninvasive techniques (e.g., such as via the IF method) one or more cardiac events occurred based on an arterial pressure waveform of a cardiac cycle of a patient. As another example, training machine learning model 750 may be selected if the analysis to be performed, using noninvasive techniques (e.g., such as via the IF method), is determining a size of an infarction. In some embodiments, operation 1106 may be performed by a subsystem that is the same or similar to model execution subsystem 114.

In operation 1208, the intrinsic frequencies, intrinsic phase angles, intrinsic envelopes, RHDN, ER, or other cardiac parameters may be provided, as input, to the trained machine learning model that was selected. In operation 1210, an indication of a size of an MI experienced by the patient, based on the cardiac parameters computed from the arterial pressure waveform, may be obtained. The indication may be for a percentage or, more generally, amount, of necrotic carotid tissue present due to the MI. Alternatively, or additionally, the mass of necrosis over total LV mass may be provided by the indication. In some embodiments, operations 1208 and 1210 may be performed by a subsystem that is the same or similar to model execution subsystem 114.

In operation 1212, a determination may be made as to whether the size of the MI satisfies a threshold condition. In some embodiments, the threshold condition may be satisfied when the size of the MI estimated by the trained machine learning model (e.g., trained machine learning model 750) is greater than or equal to a threshold size. For example, the threshold size may be 1% or more, 5% or more, 20% or more, 50% or more, or other amounts. Each threshold size refers to an amount of necrotic tissue as compared to a total amount of carotid tissue. In some cases, the threshold size may be a threshold mass, representing a mass of necrotic tissue. In some embodiments, operation 1212 may be performed by a subsystem that is the same or similar to alert generation subsystem 116.

At operation 1214, it is determined whether the threshold condition was satisfied. If so, then process 1200 may proceed to operation 1216, where an alert is generated, or, if not, process 1200 may proceed to operation 1220, where the estimated infarct size is stored in memory. In some embodiments, the alert may be a message, such as a text message, video message, image, or other message. In operation 1218, the generated alert may be provided to the patient, the patient's medical provider, or both, depending on the preferences of the patient and health privacy rules. In some embodiments, operations 1214-1220 may be performed by a subsystem that is the same or similar to alert generation subsystem 116.

Figure 13:
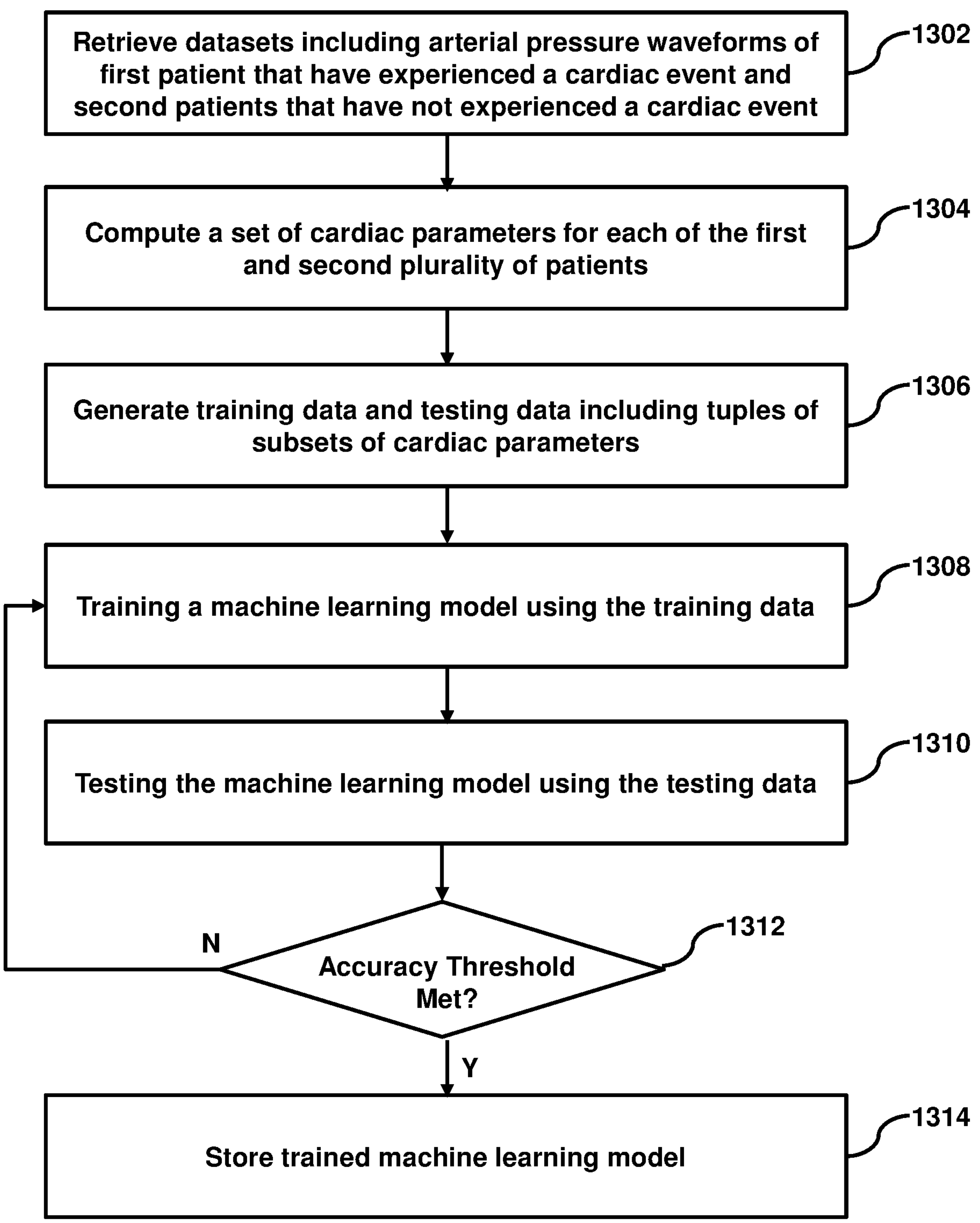
FIG. 13 illustrates an example process for training a machine learning model to determine whether a patient has experienced a cardiac event, in accordance with various embodiments.

FIG. 13 illustrates an example process for training a machine learning model to determine whether a patient has experienced a cardiac event, in accordance with various embodiments. In some embodiments, process 1300 may begin at operation 1302. In operation 1302, datasets including arterial pressure waveforms of first patients that have experienced a cardiac event and second that have not experienced a cardiac event may be retrieved. For instance, sample waveform database 138 may store waveforms for a plurality of patients, each including metadata indicating whether a respective patient experienced a cardiac event and, if so, a type of cardiac event experienced. In some embodiments, operation 1302 may be performed by a subsystem that is the same or similar to model training subsystem 118.

In operation 1304, a set of cardiac parameters for each of the first and second patients may be computed. In some embodiments, based on a given arterial pressure waveform, one or more cardiac parameters may be computed using the IF method. For example, intrinsic frequencies, intrinsic phase angles, intrinsic envelopes, or other cardiac information, may be computed from a given arterial pressure waveform of the patient. In some embodiments, operation 1304 may be performed by a subsystem that is the same or similar to model training subsystem 118.

In operation 1306, training data and testing data may be generated from the set of cardiac parameters. The training data and the testing data may include sets of tuples, each including some or all of the computed cardiac parameters. As an example, the training dating, testing data, or both, may include tuples, each including a first intrinsic frequency, $\omega_1$, a systolic intrinsic phase angle $\varphi_1$, an intrinsic envelope of systole $r_s$ and diastole $r_d$. In some embodiments, the tuples may be segmented into training data and testing data such that some of the tuples of the cardiac parameters are used for training the machine learning model, and some of the tuples of the cardiac parameters are using for validating an accuracy of the model. The training data and the testing data may be stored in training data database 134. In some embodiments, operation 1306 may be performed by a subsystem that is the same or similar to model training subsystem 118.

In operation 1308, a machine learning model (e.g., an artificial neural network (ANN)) may be trained using the training data, and in operation 1310, the machine learning model, after training, may be tested. In operation 1312, a determination may be made as to whether the accuracy of the model has been met. For example, an accuracy of the model, determined from the testing at operation 1310, may be compared to a threshold accuracy score. If the accuracy score of the model is greater than or equal to an accuracy score threshold (e.g., an 80% or greater accuracy, a 90% or greater accuracy, a 95% or greater accuracy, etc.), then process 1300 may proceed to operation 1314, where the trained machine learning may be stored. The trained machine learning model may be configured to determine whether a given set of cardiac parameters, computed from an arterial pressure waveform, indicate that a patient experienced one or more types of cardiac events (e.g., acute MI, myocardial ischemia). If not, process 1300 may return to operation 1308, where the model is trained again, having its weights, biases, and other hyperparameters adjusted based on results of an optimization function. In some embodiments, operations 1308-1314 may be performed by a subsystem that is the same or similar to model training subsystem 118.

Figure 14:
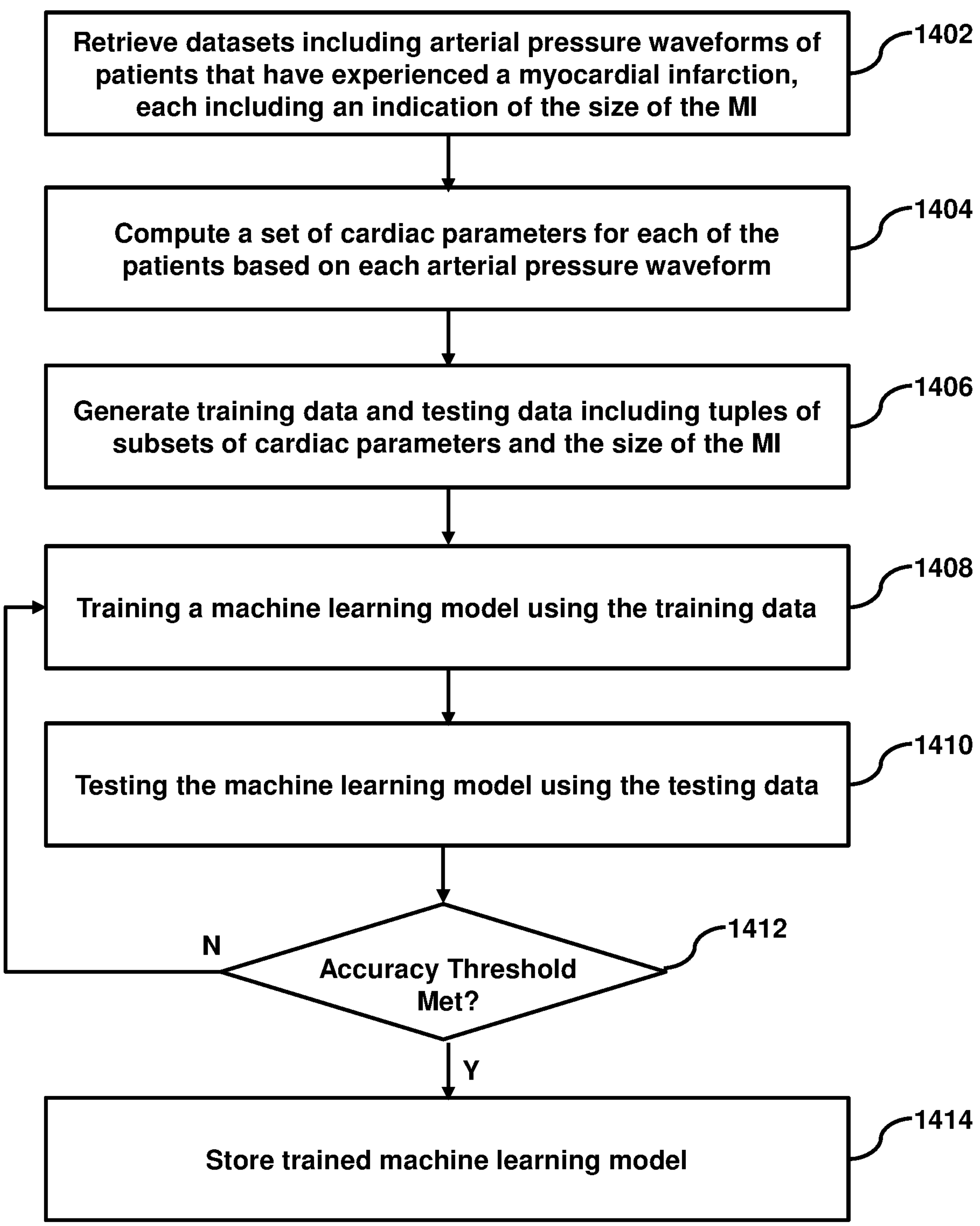
FIG. 14 illustrates an example for process for training a machine learning model to determine a size of myocardial infarction experienced by a patient, in accordance with various embodiments.

FIG. 14 illustrates an example for process for training a machine learning model to determine a size of myocardial infarction experienced by a patient, in accordance with various embodiments. In some embodiments, process 1400 may begin at operation 1402. In operation 1402, datasets including arterial pressure waveforms of patients that have experienced a cardiac event, such as an acute MI, may be obtained. In particular, the datasets may include an indication of a size of the MI, which may be represented by an amount of necrotic cardiac tissue (e.g., the mass of necrosis over total LV mass). For instance, sample waveform database 138 may store waveforms for a plurality of patients, each including metadata indicating a size of an acute MI experienced by a respective patient. In some embodiments, operation 1402 may be performed by a subsystem that is the same or similar to model training subsystem 118.

In operation 1404, a set of cardiac parameters for each of the patients may be computed. In some embodiments, based on a given arterial pressure waveform, one or more cardiac parameters may be computed using the IF method. For example, intrinsic frequencies, intrinsic phase angles, intrinsic envelopes, or other cardiac information, may be computed from a given arterial pressure waveform of the patient. In some embodiments, operation 1404 may be performed by a subsystem that is the same or similar to model training subsystem 118.

In operation 1406, training data and testing data may be generated from the set of cardiac parameters. The training data and the testing data may include sets of tuples, each including some or all of the computed cardiac parameters. As an example, the training dating, testing data, or both, may include tuples, each including a first intrinsic frequency, $\omega_1$, a systolic intrinsic phase angle $\varphi_1$, an intrinsic envelope of systole $r_s$ and diastole $r_d$. Furthermore, the tuples may include an indication of the size of the MI. In some embodiments, the tuples may be segmented into training data and testing data such that some of the tuples of the cardiac parameters are used for training the machine learning model, and some of the tuples of the cardiac parameters are using for validating an accuracy of the model. The training data and the testing data may be stored in training data database 134. In some embodiments, operation 1406 may be performed by a subsystem that is the same or similar to model training subsystem 118.

In operation 1408, a machine learning model (e.g., an artificial neural network (ANN)) may be trained using the training data, and in operation 1410, the machine learning model, after training, may be tested. In operation 1412, a determination may be made as to whether the accuracy of the model has been met. For example, an accuracy of the model, determined from the testing at operation 1410, may be compared to a threshold accuracy score. If the accuracy score of the model is greater than or equal to an accuracy score threshold (e.g., an 80% or greater accuracy, a 90% or greater accuracy, a 95% or greater accuracy, etc.), then process 1400 may proceed to operation 1414, where the trained machine learning may be stored. The trained machine learning model may be configured to determine whether a given set of cardiac parameters, computed from an arterial pressure waveform, indicate that a patient experienced one or more types of cardiac events (e.g., acute MI, myocardial ischemia). If not, process 1400 may return to operation 1408, where the model is trained again, having its weights, biases, and other hyperparameters adjusted based on results of an optimization function. In some embodiments, operations 1408-1414 may be performed by a subsystem that is the same or similar to model training subsystem 118.

Figure 15:
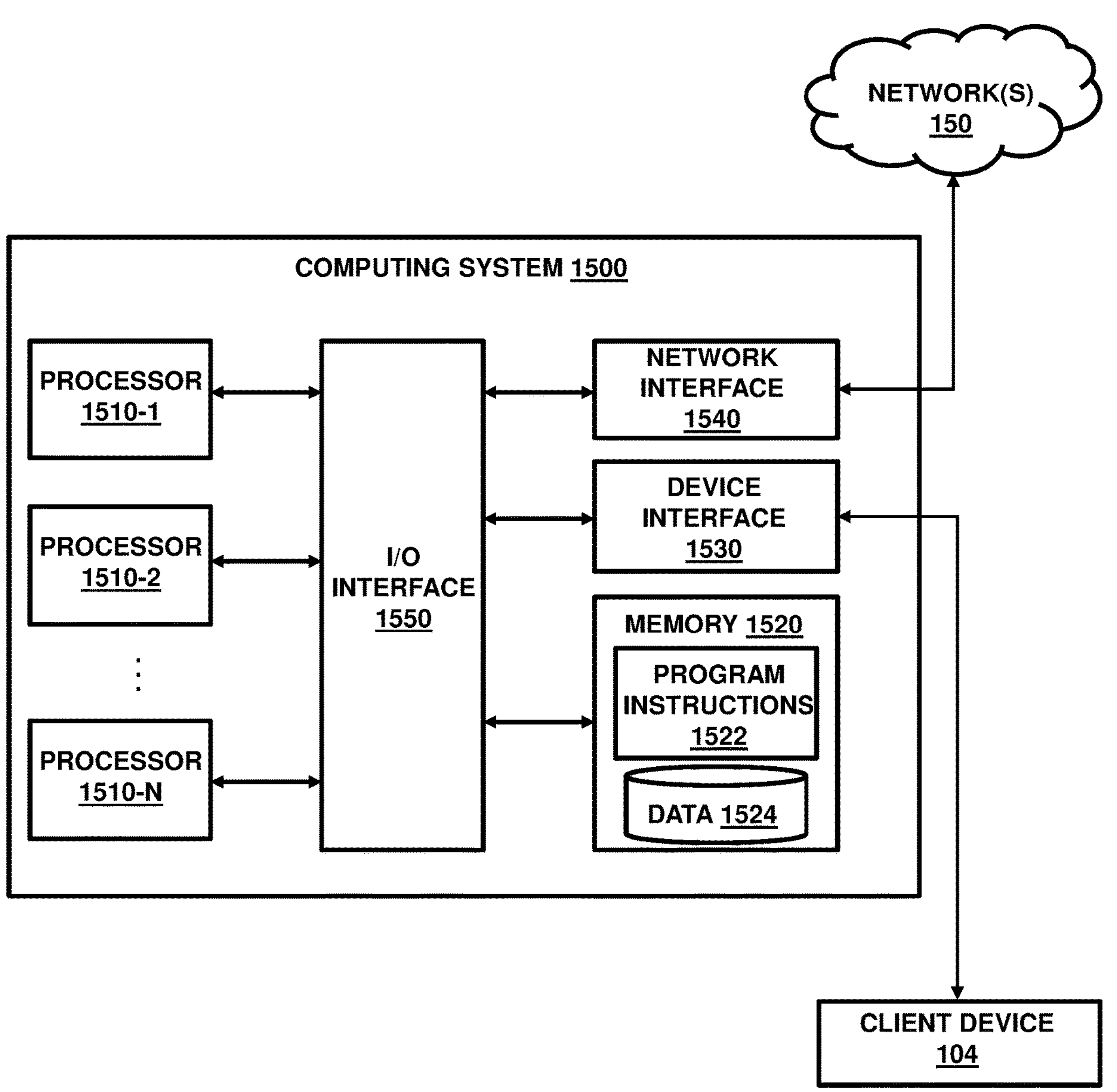
FIG. 15 is an example block diagram of a computing system upon which described program code may be executed, in accordance with various embodiments.

FIG. 15 is an example block diagram of a computing system upon which described program code may be executed, in accordance with various embodiments. Various portions of systems and methods described herein, may include or be executed on one or more computer systems similar to computing system 1500. Further, processes and modules described herein may be executed by one or more processing systems similar to that of computing system 1500.

Computing system 1500 may include one or more processors (e.g., processors 1510-1 to 1510-N) coupled to system memory 1520, an input/output I/O device interface 1530, and a network interface 1540 via an input/output (I/O) interface 1550. A processor may include a single processor or a plurality of processors (e.g., distributed processors). A processor may be any suitable processor capable of executing or otherwise performing instructions. A processor may include a central processing unit (CPU) that carries out program instructions to perform the arithmetical, logical, and input/output operations of computing system 1500. A processor may execute code (e.g., processor firmware, a protocol stack, a database management system, an operating system, or a combination thereof) that creates an execution environment for program instructions. A processor may include a programmable processor. A processor may include general or special purpose microprocessors. A processor may receive instructions and data from a memory (e.g., system memory 1520). Computing system 1500 may be a uni-processor system including one processor (e.g., processor 1510-1), or a multi-processor system including any number of suitable processors (e.g., 1510-1 to 1510-N). Multiple processors may be employed to provide for parallel or sequential execution of one or more portions of the techniques described herein. Processes, such as logic flows, described herein may be performed by one or more programmable processors executing one or more computer programs to perform functions by operating on input data and generating corresponding output. Processes described herein may be performed by, and apparatus can also be implemented as, special purpose logic circuitry, e.g., an FPGA (field programmable gate array) or an ASIC (application specific integrated circuit). Computing system 1500 may include a plurality of computing devices (e.g., distributed computer systems) to implement various processing functions.

I/O device interface 1530 may provide an interface for connection of one or more I/O devices 1560 to computing system 1500. I/O devices may include devices that receive input (e.g., from a user) or output information (e.g., to a user). I/O devices 1560 may include, for example, graphical user interface presented on displays (e.g., a cathode ray tube (CRT) or liquid crystal display (LCD) monitor), pointing devices (e.g., a computer mouse or trackball), keyboards, keypads, touchpads, scanning devices, voice recognition devices, gesture recognition devices, printers, audio speakers, microphones, cameras, or the like. I/O devices 1560 may be connected to computing system 1500 through a wired or wireless connection. I/O devices 1560 may be connected to computing system 1500 from a remote location. I/O devices 1560 located on remote computer system, for example, may be connected to computing system 1500 via a network and network interface 1540. The device interface in some embodiments can be wire connected to the client device as depicted in FIG. 15. In some other embodiments the device interface may be connected to the client device wirelessly. In some wireless embodiments, the computing system is implemented in the cloud.

Network interface 1540 may include a network adapter that provides for connection of computing system 1500 to a network. Network interface 1540 may facilitate data exchange between computing system 1500 and other devices connected to the network. Network interface 1540 may support wired or wireless communication. The network may include an electronic communication network, such as the Internet, a local area network (LAN), a wide area network (WAN), a cellular communications network, or the like.

System memory 1520 may be configured to store program instructions 1522 or data 1524. Program instructions 1522 may be executable by a processor (e.g., one or more of processors 1510-1 to 1510-N) to implement one or more embodiments of the present techniques. Instructions 1522 may include modules of computer program instructions for implementing one or more techniques described herein with regard to various processing modules. Program instructions may include a computer program (which in certain forms is known as a program, software, software application, script, or code). A computer program may be written in a programming language, including compiled or interpreted languages, or declarative or procedural languages. A computer program may include a unit suitable for use in a computing environment, including as a stand-alone program, a module, a component, or a subroutine. A computer program may or may not correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one or more computer processors located locally at one site or distributed across multiple remote sites and interconnected by a communication network.

System memory 1520 may include a tangible program carrier having program instructions stored thereon. A tangible program carrier may include a non-transitory computer readable storage medium. A non-transitory computer readable storage medium may include a machine readable storage device, a machine readable storage substrate, a memory device, or any combination thereof. Non-transitory computer readable storage medium may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. System memory 1520 may include a non-transitory computer readable storage medium that may have program instructions stored thereon that are executable by a computer processor (e.g., one or more of processors 1510-1-1510-N) to cause the subject matter and the functional operations described herein. A memory (e.g., system memory 1520) may include a single memory device and/or a plurality of memory devices (e.g., distributed memory devices). Instructions or other program code to provide the functionality described herein may be stored on a tangible, non-transitory computer readable media. In some cases, the entire set of instructions may be stored concurrently on the media, or in some cases, different parts of the instructions may be stored on the same media at different times.

I/O interface 1550 may be configured to coordinate I/O traffic between processors 1510-1 to 1510-N, system memory 1520, network interface 1540, I/O devices 1560, and/or other peripheral devices. I/O interface 1550 may perform protocol, timing, or other data transformations to convert data signals from one component (e.g., system memory 1520) into a format suitable for use by another component (e.g., processors 1510-1 to 1510-N). I/O interface 1550 may include support for devices attached through various types of peripheral buses, such as a variant of the Peripheral Component Interconnect (PCI) bus standard or the Universal Serial Bus (USB) standard.

Embodiments of the techniques described herein may be implemented using a single instance of computing system 1500 or multiple computing systems 1500 configured to host different portions or instances of embodiments. Multiple computing systems 1500 may provide for parallel or sequential processing/execution of one or more portions of the techniques described herein.

Those skilled in the art will appreciate that computing system 1500 is merely illustrative and is not intended to limit the scope of the techniques described herein. Computing system 1500 may include any combination of devices or software that may perform or otherwise provide for the performance of the techniques described herein. For example, computing system 1500 may include or be a combination of a cloud-computing system, a data center, a server rack, a server, a virtual server, a desktop computer, a laptop computer, a tablet computer, a server device, a client device, a mobile telephone, a personal digital assistant (PDA), a mobile audio or video player, a game console, a vehicle-mounted computer, or a Global Positioning System (GPS), or the like. Computing system 1500 may also be connected to other devices that are not illustrated, or may operate as a stand-alone system. In addition, the functionality provided by the illustrated components may in some embodiments be combined in fewer components or distributed in additional components. Similarly, in some embodiments, the functionality of some of the illustrated components may not be provided or other additional functionality may be available.

Those skilled in the art will also appreciate that while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-accessible medium or a portable article to be read by an appropriate drive, various examples of which are described above. In some embodiments, instructions stored on a computer-accessible medium separate from computing system 1500 may be transmitted to computing system 1500 via transmission media or signals such as electrical, electromagnetic, or digital signals, conveyed via a communication medium such as a network or a wireless link. Various embodiments may further include receiving, sending, or storing instructions or data implemented in accordance with the foregoing description upon a computer-accessible medium. Accordingly, the present techniques may be practiced with other computer system configurations.

In block diagrams, illustrated components are depicted as discrete functional blocks, but embodiments are not limited to systems in which the functionality described herein is organized as illustrated. The functionality provided by each of the components may be provided by software or hardware modules that are differently organized than is presently depicted, for example such software or hardware may be intermingled, conjoined, replicated, broken up, distributed (e.g. within a data center or geographically), or otherwise differently organized. The functionality described herein may be provided by one or more processors of one or more computers executing code stored on a tangible, non-transitory, machine readable medium. In some cases, notwithstanding use of the singular term "medium," the instructions may be distributed on different storage devices associated with different computing devices, for instance, with each computing device having a different subset of the instructions, an implementation consistent with usage of the singular term "medium" herein. In some cases, third party content delivery networks may host some or all of the information conveyed over networks, in which case, to the extent information (e.g., content) is said to be supplied or otherwise provided, the information may be provided by sending instructions to retrieve that information from a content delivery network.

The reader should appreciate that the present application describes several independently useful techniques. Rather than separating those techniques into multiple isolated patent applications, applicants have grouped these techniques into a single document because their related subject matter lends itself to economies in the application process. But the distinct advantages and aspects of such techniques should not be conflated. In some cases, embodiments address all of the deficiencies noted herein, but it should be understood that the techniques are independently useful, and some embodiments address only a subset of such problems or offer other, unmentioned benefits that will be apparent to those of skill in the art reviewing the present disclosure. Due to costs constraints, some techniques disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such techniques or all aspects of such techniques.

It should be understood that the description and the drawings are not intended to limit the present techniques to the particular form disclosed, but to the contrary, the intention is to cover all modifications, equivalents, and alternatives falling within the spirit and scope of the present techniques as defined by the appended claims. Further modifications and alternative embodiments of various aspects of the techniques will be apparent to those skilled in the art in view of this description. Accordingly, this description and the drawings are to be construed as illustrative only and are for the purpose of teaching those skilled in the art the general manner of carrying out the present techniques. It is to be understood that the forms of the present techniques shown and described herein are to be taken as examples of embodiments. Elements and materials may be substituted for those illustrated and described herein, parts and processes may be reversed or omitted, and certain features of the present techniques may be utilized independently, all as would be apparent to one skilled in the art after having the benefit of this description of the present techniques. Changes may be made in the elements described herein without departing from the spirit and scope of the present techniques as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include", "including", and "includes" and the like mean including, but not limited to. As used throughout this application, the singular forms "a," "an," and "the" include plural referents unless the content explicitly indicates otherwise. Thus, for example, reference to "an element" or "a element" includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Similarly, reference to "a computer system" performing step A and "the computer system" performing step B can include the same computing device within the computer system performing both steps or different computing devices within the computer system performing steps A and B. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every. Limitations as to sequence of recited steps should not be read into the claims unless explicitly specified, e.g., with explicit language like "after performing X, performing Y," in contrast to statements that might be improperly argued to imply sequence limitations, like "performing X on items, performing Y on the X'ed items," used for purposes of making claims more readable rather than specifying sequence. Statements referring to "at least Z of A, B, and C," and the like (e.g., "at least Z of A, B, or C"), refer to at least Z of the listed categories (A, B, and C) and do not require at least Z units in each category. Unless specifically stated otherwise, as apparent from the discussion, it is appreciated that throughout this specification discussions utilizing terms such as "processing," "computing," "calculating," "determining" or the like refer to actions or processes of a specific apparatus, such as a special purpose computer or a similar special purpose electronic processing/computing device. Features described with reference to geometric constructs, like "parallel," "perpendicular/orthogonal," "square", "cylindrical," and the like, should be construed as encompassing items that substantially embody the properties of the geometric construct, e.g., reference to "parallel" surfaces encompasses substantially parallel surfaces. The permitted range of deviation from Platonic ideals of these geometric constructs is to be determined with reference to ranges in the specification, and where such ranges are not stated, with reference to industry norms in the field of use, and where such ranges are not defined, with reference to industry norms in the field of manufacturing of the designated feature, and where such ranges are not defined, features substantially embodying a geometric construct should be construed to include those features within 15% of the defining attributes of that geometric construct. The terms "first", "second", "third," "given" and so on, if used in the claims, are used to distinguish or otherwise identify, and not to show a sequential or numerical limitation. As is the case in ordinary usage in the field, data structures and formats described with reference to uses salient to a human need not be presented in a human-intelligible format to constitute the described data structure or format, e.g., text need not be rendered or even encoded in Unicode or ASCII to constitute text; images, maps, and data-visualizations need not be displayed or decoded to constitute images, maps, and data-visualizations, respectively; speech, music, and other audio need not be emitted through a speaker or decoded to constitute speech, music, or other audio, respectively. Computer implemented instructions, commands, and the like are not limited to executable code and can be implemented in the form of data that causes functionality to be invoked, e.g., in the form of arguments of a function or API call. To the extent bespoke noun phrases (and other coined terms) are used in the claims and lack a self-evident construction, the definition of such phrases may be recited in the claim itself, in which case, the use of such bespoke noun phrases should not be taken as invitation to impart additional limitations by looking to the specification or extrinsic evidence.

In this patent, to the extent any U.S. patents, U.S. patent applications, or other materials (e.g., articles) have been incorporated by reference, the text of such materials is only incorporated by reference to the extent that no conflict exists between such material and the statements and drawings set forth herein. In the event of such conflict, the text of the present document governs, and terms in this document should not be given a narrower reading in virtue of the way in which those terms are used in other materials incorporated by reference.

While the foregoing has described what are considered to constitute the present teachings and/or other examples, it is understood that various modifications may be made thereto and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

The present techniques will be better understood with reference to the following enumerated embodiments:

A1. A method, comprising: obtaining data representing measurements of a cardiac cycle of a patient; determining, based the data, a first intrinsic frequency the cardiac cycle and a first intrinsic phase angle of the cardiac cycle; providing the first intrinsic frequency and the first intrinsic phase angle to a trained machine learning model; obtaining, from the trained machine learning model, a set of values each representing a likelihood that the patient has experienced a cardiovascular event; determining whether one or more values from the set of values satisfy a threshold condition; and storing a result of the determination of whether one or more values from the set of values satisfy the threshold condition in memory.

A2. The method of embodiment A1, wherein the method further comprises: determining a second intrinsic frequency of the cardiac cycle and a second intrinsic frequency of the cardiac cycle.

A3. The method of any one of embodiments A1-A2, wherein the method further comprises: determining an intrinsic envelope of a systolic portion of the cardiac cycle and determining an intrinsic envelope of a diastolic portion of the cardiac cycle.

A4. The method of any one of embodiments A1-A3, wherein the method further comprises: determining at least one of an envelope ratio or a relative height of the dicrotic notch.

A5. The method of any one of embodiments A1-A4, wherein the trained machine learning model is a trained artificial neural network configured to determine whether the patient experienced at least one of a plurality of cardiovascular events.

A6. The method of embodiment A5, wherein the plurality of cardiac events include an acute myocardial infarction MI and myocardial ischemia.

A7. The method of embodiment A5, wherein the plurality of cardiovascular events includes the cardiovascular event.

A8. The method of any one of embodiments A1-A7, wherein the data representing the measurements of the cardiac cycle of the first patient are obtained from a client device of the first patient.

A9. The method of embodiment A8, wherein the client device is operatively coupled to at least one sensor configured to capture the measurements of the cardiac cycle of the patient, generate the data representing the measurements of the cardiac cycle of the patient, and at least one of output or store, in memory, the data representing the measurements of the cardiac cycle of the patient.

A10. The method of any one of embodiments A8-A9, wherein the client device is a wearable device further configured to generate one or more waveforms representing the cardiac cycle of the patient based on the data representing the measurements of the cardiac cycle of the patient, wherein the first intrinsic frequency and the first intrinsic phase angle are determined based on the one or more waveforms.

A11. The method of any one of embodiments A1-A10, wherein the first intrinsic frequency and the first intrinsic phase angle are determined using steps for performing an intrinsic frequency analysis to an arterial pressure waveform.

A12. The method of any one of embodiments A1-A11, further comprising: steps for training a machine learning model to obtain the trained machine learning model.

A13. The method of any one embodiments A1-A12, further comprising: retrieving, from a database, a plurality of datasets comprising waveforms representing (i) cardiac cycles of a first plurality of patients that have experienced one or more of a plurality of cardiovascular events and (ii) cardiac cycles of a second plurality of patients that have not experienced any of the plurality of cardiovascular events; determining, for each of the first plurality of patients and the second plurality of patients, based on the waveforms representing the cardiac cycles of the first plurality of patients that have experienced the one or more of the plurality of cardiovascular events and the waveforms of the second plurality of patients that have not experienced any of the plurality of cardiovascular events, a first intrinsic frequency associated with a systolic phase of a cardiac cycle of a respective patient and a first intrinsic phase angle of the systolic phase of the cardiac cycle to obtain a plurality of first intrinsic frequencies and a plurality of systolic intrinsic phase angles respectively corresponding to the plurality of first intrinsic frequencies; generating and storing training data comprising a plurality of tuples respectively corresponding to each of the first plurality of patients and the second plurality of patients, wherein each tuple includes one of the plurality of first intrinsic frequencies and one of the plurality of systolic intrinsic phase angles, wherein each tuple of the plurality of tuples corresponds to one of the first plurality of patients or the second plurality of patients; and training and testing a neural network based on the training data to obtain the trained neural network.

A14. The method of embodiment A13, further comprising: determining a second intrinsic frequency associated with a diastolic phase of the cardiac cycle and a diastolic intrinsic phase angle associated with the diastolic phase of the cardiac cycle to obtain a plurality of second intrinsic frequencies and a plurality of diastolic intrinsic phase angles respectively corresponding to the plurality of second intrinsic frequencies.

A15. The method of embodiment A14, wherein the plurality of tuples from the training data further comprises: the plurality of second intrinsic frequencies and the plurality of diastolic intrinsic phase angles.

A16. The method of any one embodiments A13-A15, further comprising: computing at least one of an intrinsic envelope of systole, an intrinsic envelope of diastole, an envelope ratio, or a relative height of the dicrotic notch (RHDN), wherein the tuples further include the at least one of the intrinsic envelope of systole, the intrinsic envelope of diastole, the envelope ratio, or the RHDN.

A17. The method of any one of embodiments A13-A16, wherein each tuple includes a label indicating whether a waveform of a corresponding patient refers to one of the first plurality of patients that have experienced one or more of the plurality of cardiovascular events or to one of the second plurality of patients that have not experienced any of the plurality of cardiovascular events.

A18. The method of any one of embodiments A1-A17, wherein the trained machine learning model comprises at least an input layer, one or more hidden layers, and an output layer.

A19. The method of embodiment A18, wherein nodes of the one or more hidden layers are fully connected to nodes of the input layer, the one or more hidden layers being configured to generate a classification vector comprising the set of values, each of the set of values being a classification score representing a likelihood that the first patient has experienced one of the plurality of cardiovascular events.

A20. The method of embodiment A19, wherein a last hidden layer or the output layer include a Softmax layer where a Softmax function is applied to the classification vector to determine whether the one or more values from the set of values satisfy the threshold condition.

A21. The method of any one of embodiments A1-A20, wherein the threshold condition being satisfied comprises a given value from the set of values being greater than or equal to a threshold value.

A22. The method of any one of embodiments A1-A21, further comprising: responsive to determining that the one or more values from the set of values satisfy the threshold condition, generating an alert indicating that the patient has experienced a cardiac event; and providing the alert to one or more client devices of the patient, a medical provider of the patient, or the patient and the medical provider of the patient.

A23. The method of any one of embodiments A1-A22, wherein the data representing the measurements of the cardiac cycle of the patient are captured using cardiovascular measurement means.

A24. The method of any one of embodiments A1-A23, wherein the method is performed locally on a client device of the patient.

A25. The method of any one of embodiments A1-A24, wherein the cardiovascular event occurred within a predetermined amount of time of the measurements being captured by a client device of the patient.

B1. A method, comprising: obtaining first data representing a hemodynamic waveform of a patient that experienced a myocardial infarction (MI); determining, based on the first data, a set of cardiovascular parameters of the patient, the set of cardiovascular parameters comprising a first intrinsic frequency of a cardiac cycle of the patient, a first intrinsic phase angle of the cardiac cycle, a relative height of a dicrotic notch (RHDN) of the cardiac cycle, and an envelope ratio (ER) of the cardiac cycle; providing the set of cardiovascular parameters to a trained machine learning model configured to determine a size of a myocardial infarction experienced by the patient; obtaining, from the trained machine learning model, the size of the myocardial infarction experienced by the patient; and providing second data comprising the size of the myocardial infarction experienced by the patient to one or more client devices of the patient, a medical provider of the patient, or the patient and the medical provider of the patient.

B2. The method of embodiment B1, wherein the set of cardiovascular parameters further comprises a second intrinsic frequency of the cardiac cycle, and a second intrinsic phase angle of the cardiac cycle.

B3. The method of any one of embodiments B1-B2, wherein the set of cardiovascular parameters further comprise an intrinsic envelope of a systolic portion of the cardiac cycle and an intrinsic envelope of a diastolic portion of the cardiac cycle.

B4. The method of any one of embodiments B1-B3, wherein the set of cardiovascular parameters are computed by performing steps for applying the intrinsic frequency method to an arterial pressure waveform.

B5. The method of any one of embodiments B2-B4, wherein: the first intrinsic frequency describes a systolic phase of the cardiac cycle of the patient; the second intrinsic frequency describes a diastolic phase of the cardiac cycle of the patient; the first intrinsic phase angle comprises a systolic intrinsic phase angle describing the systolic phase of the cardiac cycle of the patient; and the second intrinsic phase angle comprises a diastolic intrinsic phase angle describing the diastolic phase of the cardiac cycle of the patient.

B6. The method of any one of embodiments B1-B5, wherein the hemodynamic waveform of the patient comprises at least one of an arterial pressure waveform or a vessel wall displacement waveform.

B7. The method of any one of embodiments B1-B6, wherein the trained machine learning model is a trained artificial neural network configured to determine a size of a myocardial infarction experienced by the patient.

B8. The method of any one of embodiments B1-B7, wherein the data representing the measurements of the cardiac cycle of the first patient are obtained from a client device of the first patient.

B9. The method of embodiment B8, wherein the client device is operatively coupled to at least one sensor configured to capture the measurements of the cardiac cycle of the patient, generate the data representing the measurements of the cardiac cycle of the patient, and at least one of output or store, in memory, the data representing the measurements of the cardiac cycle of the patient.

B10. The method of any one of embodiments B8-B9, wherein the client device is a wearable device further configured to generate one or more waveforms representing the cardiac cycle of the patient based on the data representing the measurements of the cardiac cycle of the patient, wherein the first intrinsic frequency and the first intrinsic phase angle are determined based on the one or more waveforms.

B11. The method of any one of embodiments B1-B10, wherein the first intrinsic frequency and the first intrinsic phase angle are determined using steps for performing an intrinsic frequency analysis to an arterial pressure waveform.

B12. The method of any one of embodiments B1-B11, further comprising: steps for training a machine learning model to obtain the trained machine learning model.

B13. The method of any one of embodiments B1-B12, further comprising: retrieving a plurality of hemodynamic waveforms, each of the plurality of hemodynamic waveforms respectively corresponding to one of a plurality of patients, each of whom have experienced an acute myocardial infarction; determining, for each of the plurality of hemodynamic waveforms, a set of cardiovascular parameters of a cardiac cycle of a respective one of the plurality of patients to obtain a plurality of sets of cardiovascular parameters, wherein each set of cardiovascular parameters of the plurality of sets of cardiovascular parameters comprises: (i) one or more intrinsic frequencies of the cardiac cycle of the respective one of the plurality of patients, (ii) one or more intrinsic phase angles of the cardiac cycle of the respective one of the plurality of patients, (iii) a relative height of a dicrotic notch (RHDN) of the cardiac cycle of the respective one of the plurality of patients, and (iv) an envelope ratio (ER) of the cardiac cycle of the respective one of the plurality of patients; generating and storing training data comprising tuples of the one or more intrinsic frequencies, the one or more intrinsic phase angles, the RHDN, and the ER for each of the plurality of patients, wherein each tuple includes an indication of a size of a myocardial infarction experienced by the respective one of the plurality of patients; and training and testing a neural network based on the training data to obtain the trained neural network.

B14. The method of embodiment B13, wherein the set of cardiac parameters further includes at least one of an intrinsic envelope of systole or an intrinsic envelope of diastole.

B15. The method of any one of embodiments B13-B14, wherein the plurality of tuples from the training data further each include comprises: at least one of a first intrinsic frequency of a systolic portion of the cardiac cycle or a second intrinsic frequency of a diastolic portion of the cardiac cycle, at least one of a systolic intrinsic phase angle of the systolic portion of the cardiac cycle or a diastolic phase angle of the diastolic portion of the cardiac cycle, at least one of an intrinsic envelope of the systolic portion of the cardiac cycle or an intrinsic envelope of the diastolic portion of the cardiac cycle, the ER for the cardiac cycle, and the RHDN of the cardiac cycle.

B16. The method of any one of embodiments B13-B15, wherein each tuple includes a label indicating a size of an infarction that a corresponding patient experienced.

B17. The method of any one of embodiments B1-B16, wherein the first data representing the hemodynamic waveform of a patient are obtained from a client device of the patient.

B18. The method of embodiment B17, wherein the client device is operatively coupled to at least one sensor configured to capture hemodynamic measurements of the cardiac cycle of the patient, generate the first data representing the hemodynamic waveform of the cardiac cycle of the patient, and at least one of output or store, in memory, the first data representing the hemodynamic waveform of the cardiac cycle of the patient.

B19. The method of embodiment B18, wherein the client device is a wearable device.

B20. The method of any one of embodiments B1-B19, wherein the trained machine learning model comprises at least an input layer, one or more hidden layers, and an output layer.

B21. The method of embodiment B20, wherein nodes of the one or more hidden layers are fully connected to nodes of the input layer, the one or more hidden layers being configured to generate a value indicating an estimated size of a myocardial infarction experienced by a patient.

B22. The method of any one of embodiments B1-B21, further comprising: updating training data used to train the trained machine learning model based on the set of cardiovascular parameters and the size of myocardial infarction of the patient to obtain updated training data, wherein the updated training data comprises a tuple including the set of cardiovascular parameters and the size of the myocardial infarction of the patient.

B23. The method of any one of embodiments B1-B22, further comprising: steps for training a trained neural network to obtain the trained neural network.

B24. The method of any one of embodiments B1-B23, wherein the first data representing the hemodynamic waveform of the patient are captured using cardiovascular measurement means.

B25. The method of any one of embodiments B1-B24, further comprising: responsive to determining that the size of the myocardial infarction satisfies a threshold condition, generating an alert indicating that the patient has experienced an acute MI and the size of the acute MI; and providing the alert to one or more client devices of the patient, a medical provider of the patient, or the patient and the medical provider of the patient.

B26. The method of any one of embodiments B1-B25, wherein the first data representing the measurements of the cardiac cycle of the patient are captured using cardiovascular measurement means.

B27. The method of any one of embodiments B1-B26, wherein the method is performed locally on a client device of the patient.

B28. The method of any one of embodiments B1-B27, wherein the myocardial infarction experienced by the patient occurred within a predetermined amount of time of the measurements being captured by a client device of the patient.

C1. A system comprising: memory storing computer program instructions; and one or more processors configured to execute the computer program instructions such that, when executed, the one or more processors effectuate operations comprising the method of any one of embodiments A1-A25 or B1-B28.

C2. A non-transitory computer-readable medium storing computer program instructions that, when executed by one or more processors of a computing system, effectuate operations comprising the method of any one of embodiments A1-A25 or B1-B28.

What is claimed is:

1. A system for detecting myocardial infarction and ischemia using non-invasive tests, the system comprising:

a wearable device worn by a patient comprising at least one sensor configured to capture a set of arterial blood pressure measurements of the patient, the wearable device being further configured to generate an arterial pressure waveform representing the set of arterial blood pressure measurements;

a computing system comprising one or more processors executing computer program instructions to effectuate operations comprising:

retrieving, from a database, a plurality of datasets comprising (i) first arterial pressure waveforms of a first plurality of patients that have experienced a myocardial infarction and (ii) second arterial pressure waveforms of a second plurality of patients that have not experienced a myocardial infarction;

computing, for each of the first plurality of patients and each of the second plurality of patients, a respective first intrinsic frequency, a respective second intrinsic frequency, a respective systolic intrinsic phase angle, and a respective diastolic intrinsic phase angle to obtain a plurality of first intrinsic frequencies, a plurality of second intrinsic frequencies, a plurality of systolic intrinsic phase angles, a plurality of diastolic intrinsic phase angles, respectively;

generating and storing training data based on one or more of the plurality of first intrinsic frequencies, the plurality of second intrinsic frequencies, the plurality of systolic intrinsic phase angles, and the plurality of diastolic intrinsic phase angles corresponding to one of the first plurality of patients or the second plurality of patients;

training and testing an artificial neural network (ANN) implemented on the computing system based on the training data to obtain the trained ANN;

obtaining, from the wearable device, data comprising the arterial pressure waveform, wherein the arterial pressure waveform is a time-varying physiological signal corresponding to a cardiac cycle of the patient;

segmenting the arterial pressure waveform into a systolic portion and a diastolic portion based on a dicrotic notch of the arterial pressure waveform;

computing, based on the data representing the arterial pressure waveform and using an intrinsic frequency analysis constrained by continuity and periodicity conditions of the arterial pressure waveform, a first intrinsic frequency of a systolic phase of the cardiac cycle of the patient, and a second intrinsic frequency of a diastolic phase of the cardiac cycle of the patient, wherein the intrinsic frequency analysis comprises fitting a piecewise sinusoidal model to the arterial pressure waveform across the cardiac cycle, the piecewise sinusoidal model including a first component for the systolic phase and a second component for the diastolic phase, and determining the first intrinsic frequency and the second intrinsic frequency by minimizing a difference between the arterial pressure waveform and the piecewise sinusoidal model;

determining, based on the first intrinsic frequency and the second intrinsic frequency, respectively, from the intrinsic frequency analysis, a systolic intrinsic phase angle describing the systolic phase of the cardiac cycle of the patient and a diastolic intrinsic phase angle describing the diastolic phase of the cardiac cycle of the patient, wherein the systolic intrinsic phase angle is determined as a phase parameter of the first component associated with the first intrinsic frequency, and the diastolic intrinsic phase angle is determined as a phase parameter of the second component associated with the second intrinsic frequency;

providing a set of derived cardiac parameters including the first intrinsic frequency, the second intrinsic frequency, the systolic intrinsic phase angle, and the diastolic intrinsic phase angle to the trained ANN configured to generate a classification score representing a likelihood that the patient has experienced a myocardial infarction;

obtaining, from the trained ANN, a numerical value representing the classification score;

determining, based on the classification score, whether the patient has suffered the myocardial infarction; and responsive to determining that the patient has suffered the myocardial infarction, providing an alert to one or more client devices of the patient, a medical provider of the patient, or the patient and the medical provider of the patient.

2. The system of claim 1, wherein the generating and storing training data comprises a plurality of tuples of one of the plurality of first intrinsic frequencies, one of the plurality of second intrinsic frequencies, one of the plurality of systolic intrinsic phase angles, and one of the plurality of diastolic intrinsic phase angles, wherein each tuple of the plurality of tuples corresponds to one of the first plurality of patients or the second plurality of patients.

3. The system of claim 1, wherein the wearable device is further configured to capture a set of pulse-oxygen level measurements of the patient, and generate a pulse-oxygen level waveform representing the set of pulse-oxygen level measurements, the operations further comprise:

obtaining, from the wearable device, additional data comprising the pulse-oxygen level waveform;

computing, based on the additional data representing the pulse-oxygen level waveform, the first intrinsic frequency, the second intrinsic frequency, the systolic intrinsic phase angle describing the systolic phase of the cardiac cycle of the patient, and the diastolic intrinsic phase angle describing the diastolic phase of the cardiac cycle of the patient.

4. The system of claim 1, wherein the trained ANN comprises a plurality of layers including an input layer, one or more hidden layers, and an output layer, wherein the one or more hidden layers generate a classification vector comprising a set of classification scores each representing a likelihood that the patient has experienced one or more of a plurality of cardiac events, the plurality of cardiac events including myocardial infarction, and the output layer including application of a Softmax function to determine, from the set of classification scores, a value representing a probability that a set of inputs comprising the first intrinsic frequency, the second intrinsic frequency, the systolic intrinsic phase angle, and the diastolic intrinsic phase angle computed based on the arterial pressure waveform indicate that the patient has experienced one of the plurality of cardiac events.

5. A non-transitory computer-readable medium storing computer program instructions that, when executed by one or more processors of a computing system, effectuate operations comprising:

retrieving, from a database, a plurality of datasets comprising waveforms representing (i) cardiac cycles of a first plurality of patients that have experienced at least one of a plurality of cardiovascular events and (ii) cardiac cycles of a second plurality of patients that have not experienced any of the plurality of cardiovascular events;

determining, for each of the first plurality of patients and the second plurality of patients, based on the waveforms representing the cardiac cycles of the first plurality of patients that have experienced at least one of the plurality of cardiovascular events and the waveforms of the second plurality of patients that have not experienced any of the plurality of cardiovascular events, a respective first intrinsic frequency associated with a systolic phase of a cardiac cycle of a respective patient, a respective second intrinsic frequency associated with a diastolic phase of the cardiac cycle, a respective systolic intrinsic phase angle associated with the systolic phase of the cardiac cycle, and a respective diastolic intrinsic phase angle associated with the diastolic phase of the cardiac cycle to obtain a plurality of first intrinsic frequencies, a plurality of second intrinsic frequencies, a plurality of systolic intrinsic phase angles respectively corresponding to the plurality of first intrinsic frequencies, and a plurality of diastolic intrinsic phase angles respectively corresponding to the plurality of second intrinsic frequencies, respectively;

generating and storing training data based on one or more of the plurality of first intrinsic frequencies, the plurality of second intrinsic frequencies, the plurality of systolic intrinsic phase angles, and the plurality of diastolic intrinsic phase angles corresponding to one of the first plurality of patients or the second plurality of patients;

training and testing a neural network implemented on the computing system based on the training data to obtain the trained neural network;

obtaining, with the computing system, data comprising an arterial pressure waveform representing measurements of a cardiac cycle of a first patient, wherein the arterial pressure waveform is a time-varying physiological signal corresponding to the cardiac cycle of the first patient;

segmenting the arterial pressure waveform into a systolic portion and a diastolic portion based on a dicrotic notch of the arterial pressure waveform;

computing, based on the data comprising the arterial pressure waveform and using an intrinsic frequency analysis constrained by continuity and periodicity conditions of the arterial pressure waveform, a first intrinsic frequency of a systolic phase of the cardiac cycle of the first patient, and a second intrinsic frequency of a diastolic phase of the cardiac cycle of the first patient, wherein the intrinsic frequency analysis comprises fitting a piecewise sinusoidal model to the arterial pressure waveform across the cardiac cycle, the piecewise sinusoidal model including a first component for the systolic phase and a second component for the diastolic phase, and determining the first intrinsic frequency and the second intrinsic frequency by minimizing a difference between the arterial pressure waveform and the piecewise sinusoidal model;

determining, based on the first intrinsic frequency and the second intrinsic frequency, respectively, from the intrinsic frequency analysis, a systolic intrinsic phase angle describing the systolic phase of the cardiac cycle of the first patient and a diastolic intrinsic phase angle describing the diastolic phase of the cardiac cycle of the first patient, wherein the systolic intrinsic phase angle is determined as a phase parameter of the first component associated with the first intrinsic frequency, and the diastolic intrinsic phase angle is determined as a phase parameter of the second component associated with the second intrinsic frequency;

providing a set of derived cardiac parameters including the first intrinsic frequency, the second intrinsic frequency, the systolic intrinsic phase angle, and the diastolic intrinsic phase angle to the trained neural network configured to determine whether the first patient has suffered at least one of the plurality of cardiovascular events;

obtaining, from the trained neural network, a set of values each representing a likelihood that the first patient has suffered at least one of the plurality of cardiovascular events;

determining whether one or more values from the set of values satisfy a threshold condition; and storing a result of the determination of whether one or more values from the set of values satisfy the threshold condition in memory.

6. The non-transitory computer-readable medium of claim 5, wherein the data representing the measurements of the cardiac cycle of the first patient are obtained from a client device of the first patient, wherein the client device is operatively coupled to at least one sensor configured to capture the measurements of the cardiac cycle of the first patient, generate the data representing the measurements of the cardiac cycle of the first patient, and at least one of output or store, in memory, the data representing the measurements of the cardiac cycle of the first patient.

7. The non-transitory computer-readable medium of claim 6, wherein the client device is a wearable device being further configured to generate one or more waveforms, including the arterial pressure waveform, representing the cardiac cycle of the first patient based on the data representing the measurements of the cardiac cycle of the first patient, wherein the first intrinsic frequency and the second intrinsic frequency are determined based on the one or more waveforms.

8. The non-transitory computer-readable medium of claim 5, wherein the generating and storing training data comprises a plurality of tuples respectively corresponding to each of the first plurality of patients and the second plurality of patients, wherein each tuple includes one of the plurality of first intrinsic frequencies, one of the plurality of second intrinsic frequencies, one of the plurality of systolic intrinsic phase angles, and one of the plurality of diastolic intrinsic phase angles, wherein each tuple of the plurality of tuples corresponds to one of the first plurality of patients or the second plurality of patients.

9. The non-transitory computer-readable medium of claim 8, wherein each tuple includes a label indicating whether a waveform of a corresponding patient refers to one of the first plurality of patients that have experienced at least one of the plurality of cardiovascular events or to one of the second plurality of patients that have not experienced any of the plurality of cardiovascular events.

10. The non-transitory computer-readable medium of claim 5, wherein the trained neural network comprises at least an input layer, one or more hidden layers fully connected to the input layer, and an output layer, wherein the one or more hidden layers generate a classification vector comprising the set of values, each of the set of values being a classification score representing a likelihood that the first patient has experienced at least one of the plurality of cardiovascular events, and the output layer including application of a Softmax function to determine whether the one or more values from the set of values satisfy the threshold condition.

11. The non-transitory computer-readable medium of claim 5, wherein the threshold condition being satisfied comprises a given value from the set of values being greater than a threshold value.

12. The non-transitory computer-readable medium of claim 5, wherein the operations further comprise:

responsive to determining that the one or more values from the set of values satisfy the threshold condition, generating an alert indicating that the first patient has experienced a cardiac event; and providing the alert to one or more client devices of the first patient, a medical provider of the first patient, or the first patient and the medical provider of the first patient.

13. The non-transitory computer-readable medium of claim 5, wherein the data representing the measurements of the cardiac cycle of the first patient are captured using cardiovascular measurement means.

14. A method implemented by a computing system executing computer program instructions, the method comprising:

retrieving, from a database, a plurality of datasets comprising waveforms representing (i) cardiac cycles of a first plurality of patients that have experienced at least one of a plurality of cardiovascular events and (ii) cardiac cycles of a second plurality of patients that have not experienced any of the plurality of cardiovascular events;

determining, for each of the first plurality of patients and the second plurality of patients, based on the waveforms representing the cardiac cycles of the first plurality of patients that have experienced at least one of the plurality of cardiovascular events and the waveforms of the second plurality of patients that have not experienced any of the plurality of cardiovascular events, a respective first intrinsic frequency associated with a systolic phase of a cardiac cycle of a respective patient, a respective second intrinsic frequency associated with a diastolic phase of the cardiac cycle, a respective systolic intrinsic phase angle associated with the systolic phase of the cardiac cycle, and a respective diastolic intrinsic phase angle associated with the diastolic phase of the cardiac cycle to obtain a plurality of first intrinsic frequencies, a plurality of second intrinsic frequencies, a plurality of systolic intrinsic phase angles respectively corresponding to the plurality of first intrinsic frequencies, and a plurality of diastolic intrinsic phase angles respectively corresponding to the plurality of second intrinsic frequencies, respectively;

generating and storing training data based on one or more of the plurality of first intrinsic frequencies, the plurality of second intrinsic frequencies, the plurality of systolic intrinsic phase angles, and the plurality of diastolic intrinsic phase angles corresponding to one of the first plurality of patients or the second plurality of patients;

training and testing a neural network implemented on the computing system based on the training data to obtain the trained neural network;

obtaining, with the computing system, data comprising an arterial pressure waveform representing measurements of a cardiac cycle of a first patient, wherein the arterial pressure waveform is a time-varying physiological signal corresponding to the cardiac cycle of the first patient;

segmenting the arterial pressure waveform into a systolic portion and a diastolic portion based on a dicrotic notch of the arterial pressure waveform;

computing, based on the data comprising the arterial pressure waveform and using an intrinsic frequency analysis constrained by continuity and periodicity conditions of the arterial pressure waveform, a first intrinsic frequency of a systolic phase of the cardiac cycle of the first patient, and a second intrinsic frequency of a diastolic phase of the cardiac cycle of the first patient, wherein the intrinsic frequency analysis comprises fitting a piecewise sinusoidal model to the arterial pressure waveform across the cardiac cycle, the piecewise sinusoidal model including a first component for the systolic phase and a second component for the diastolic phase, and determining the first intrinsic frequency and the second intrinsic frequency by minimizing a difference between the arterial pressure waveform and the piecewise sinusoidal model;

determining, based on the first intrinsic frequency and the second intrinsic frequency, respectively, from the intrinsic frequency analysis, a systolic intrinsic phase angle describing the systolic phase of the cardiac cycle of the first patient and a diastolic intrinsic phase angle describing the diastolic phase of the cardiac cycle of the first patient, wherein the systolic intrinsic phase angle is determined as a phase parameter of the first component associated with the first intrinsic frequency, and the diastolic intrinsic phase angle is determined as a phase parameter of the second component associated with the second intrinsic frequency;

providing, with the computing system, the first intrinsic frequency, the second intrinsic frequency, the systolic intrinsic phase angle, and the diastolic intrinsic phase angle to the trained neural network configured to determine whether the first patient has suffered at least one of the plurality of cardiovascular events;

obtaining, with the computing system, from the trained neural network, a set of values each representing a likelihood that the first patient has suffered at least one of the plurality of cardiovascular events;

determining, with the computing system, whether one or more values from the set of values satisfy a threshold condition; and storing, with the computing system, a result of the determination of whether one or more values from the set of values satisfy the threshold condition in memory.

15. The method of claim 14, wherein the obtaining of the data representing the measurements of the cardiac cycle of the first patient comprises obtaining said data from a client device of the first patient, wherein the client device is operatively coupled to at least one sensor configured to capture the measurements of the cardiac cycle of the first patient, generate the data representing the measurements of the cardiac cycle of the first patient, and at least one of output or store, in memory, the data representing the measurements of the cardiac cycle of the first patient.

16. The method of claim 15, wherein the client device is a wearable device being further configured to generate one or more waveforms, including the arterial pressure waveform, representing the cardiac cycle of the first patient based on the data representing the measurements of the cardiac cycle of the first patient, wherein the first intrinsic frequency and the second intrinsic frequency are determined based on the one or more waveforms.

17. The method according to claim 14, wherein the generating and storing training data comprises a plurality of tuples respectively corresponding to each of the first plurality of patients and the second plurality of patients, wherein each tuple includes one of the plurality of first intrinsic frequencies, one of the plurality of second intrinsic frequencies, one of the plurality of systolic intrinsic phase angles, and one of the plurality of diastolic intrinsic phase angles, wherein each tuple of the plurality of tuples corresponds to one of the first plurality of patients or the second plurality of patients.

18. The method of claim 17, wherein each tuple includes a label indicating whether a waveform of a corresponding patient refers to one of the first plurality of patients that have experienced at least one of the plurality of cardiovascular events or to one of the second plurality of patients that have not experienced any of the plurality of cardiovascular events.

19. The method of claim 14, wherein the trained neural network comprises at least an input layer, one or more hidden layers fully connected to the input layer, and an output layer, wherein the one or more hidden layers generate a classification vector comprising the set of values, each of the set of values being a classification score representing a likelihood that the first patient has experienced at least one of the plurality of cardiovascular events, and the output layer including application of a Softmax function to determine whether the one or more values from the set of values satisfy the threshold condition.

20. The method of claim 14, wherein the data representing the measurements of the cardiac cycle of the first patient are captured using cardiovascular measurement means.

* * * * *